US011549103B2

(12) United States Patent
Nagaraju et al.

(10) Patent No.: US 11,549,103 B2
(45) Date of Patent: Jan. 10, 2023

(54) RECOMBINANT MICROORGANISMS AND METHODS OF USE THEREOF

(71) Applicant: LanzaTech NZ, Inc., Skokie, IL (US)

(72) Inventors: Shilpa Nagaraju, Skokie, IL (US);
Bakir Al-Sinawi, Sydney (AU);
Sashini De Tissera, Skokie, IL (US);
Michael Koepke, Skokie, IL (US)

(73) Assignee: LanzaTech NZ, Inc., Skokie, IL (US)

( * ) Notice: Subject to any disclaimer, the term of this patent is extended or adjusted under 35 U.S.C. 154(b) by 0 days.

(21) Appl. No.: 16/856,841

(22) Filed: Apr. 23, 2020

(65) Prior Publication Data

US 2020/0248152 A1 Aug. 6, 2020

Related U.S. Application Data

(62) Division of application No. 14/609,420, filed on Jan. 29, 2015, now abandoned.

(60) Provisional application No. 61/933,815, filed on Jan. 30, 2014, provisional application No. 61/944,541, filed on Feb. 25, 2014.

(51) Int. Cl.
| | |
|---|---|
| *C12P 7/06* | (2006.01) |
| *C12P 7/24* | (2006.01) |
| *C12P 13/06* | (2006.01) |
| *C12N 9/04* | (2006.01) |
| *C12N 15/52* | (2006.01) |
| *C12P 7/54* | (2006.01) |
| *C12P 7/18* | (2006.01) |

(52) U.S. Cl.
CPC ........... *C12N 9/0006* (2013.01); *C12N 15/52* (2013.01); *C12P 7/065* (2013.01); *C12P 7/18* (2013.01); *C12P 7/54* (2013.01); *Y02E 50/10* (2013.01)

(58) Field of Classification Search
CPC ...... C12N 9/88; C12N 9/0008; C12N 9/1029; C12P 7/06; C12P 7/649
USPC ..... 435/160, 141, 146, 106, 161, 139, 252.7
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 6,368,819 B1 | 4/2002 | Gaddy et al. | |
| 2009/0042265 A1 | 2/2009 | Atkinson et al. | |
| 2011/0229947 A1 | 9/2011 | Zahn et al. | |
| 2013/0157322 A1 | 6/2013 | Simpson et al. | |
| 2013/0323820 A1 | 12/2013 | Chen et al. | |

FOREIGN PATENT DOCUMENTS

| | | |
|---|---|---|
| WO | 2002008438 A2 | 1/2002 |
| WO | 2008028055 A2 | 3/2008 |
| WO | 2009064200 A2 | 5/2009 |
| WO | 2011116358 A2 | 9/2011 |
| WO | 2012015317 A1 | 2/2012 |
| WO | 2012053905 A1 | 4/2012 |
| WO | 2012105853 A1 | 8/2012 |
| WO | 2012112416 A2 | 8/2012 |
| WO | 2012109578 A3 | 11/2012 |
| WO | 2013115659 A2 | 8/2013 |

OTHER PUBLICATIONS

Guo et al. (Biotechnol biofuels 2014, 7(44) pp. 1-11.*
Mohr, PLoS One, 2013, vol. 8, No. 7, pp. 1-15.
Furdui, Cristina et al., The Role of Pyruvate Ferredoxin Oxidoreductase in Pyruvate Synthesis during Autotrophic Growth by the Wood-Ljungdahl Pathway, The Journal of Biological Chemistry, vol. 275, No. 37, Sep. 15, 2000, pp. 28494-28499.
Kita, J Biosci Bioeng, 115: 347-352, 2013.
Bengelsdorf, Environ Technol, 34:1639-1651, 2013.
International Search Report for International Patent Application PCT/US2015/013625, Korean Intellectual Property Office, dated Apr. 29, 2015.
Kopke, Reconstruction of an acetogenic 2,3-butanediol pathway involving a novel NADPH-dependent primarysecondary alcohol dehydrogenase, Appl Environ Microbiol, published online Mar. 21, 2014.
Burk, Biotechnology for chemical production: challenges and opportunities, Trends in Biotechnology, Mar. 2016, vol. 34, No. 3, pp. 187-190.
Abrini, Arch Microbiol, 161: 345-351, 1994.
Drake, The Prokaryotes, 354-420, Springer, New York, NY, 2006.
Heap, J Microbiol Methods, 70: 452-464, 2007.
Heiskanen, Enzyme Microb Technol, 41 362-367,2007.
Hensirisak, Appl Biochem Biotechnol, 101: 211-227, 2002.
Herbert, FEMS Microbiol Lett, 229: 103-110, 2003.
Huh, Proc Biochem 41:1461-1465, 2006.
Hungate, Methods Microbiol, 3B: 117-132, 1969.
Jennert, Microbiol, 146: 3071-3080, 2000.
Köpke, PNAS USA, 107:13087-13092, 2010.
Köpke, Appl Environ Microbiol, 77: 5467-5475, 2011.
Köpke, Curr Opin Biotechnol, 22: 320-325, 2011.

(Continued)

*Primary Examiner* — Tekchand Saidha
*Assistant Examiner* — Mohammad Y Meah
(74) *Attorney, Agent, or Firm* — Stephen M. Chong

(57) ABSTRACT

Provided is a method of producing a product by culturing a carboxydotrophic acetogenic bacterium with a disrupting mutation in a lactate dehydrogenase enzyme in the presence of a substrate comprising CO, $CO_2$, and/or $H_2$. Preferably, the disrupting mutation reduces or eliminates the expression or activity of the enzyme such that the bacterium produces a reduced amount of lactate or no lactate.

11 Claims, 6 Drawing Sheets
Specification includes a Sequence Listing.

(56) References Cited

OTHER PUBLICATIONS

Leang, Applied Environ Microbiol, 79:1102-1109,2013.
Lee, Appl Microbiol Biotechnol, 79: 11-22, 2008.
Mermelstein, Biotechnol, 10: 190-195, 1992.
Murray, Microbiol Molec Biol Rev, 64:412-434,2000.
Parthasarathy, Development of a Genetic Modification System in Clostridium scatologenes ATCC 25775 for Generation of Mutants, Masters Project, Western Kentucky University, 2010.
Perez, Biotechnol Bioeng, 110:1066-1077,2012.
Ragsdale, Biochim Biophys Acta, 1784: 1873-1898, 2008.
Schiel-Bengelsdorf, Synthetic Biol, 15: 2191-2198, 2012.
Song, Enzyme Microb Technol, 39: 352-361, 2006.
Stratz, Appl Environ Microbiol, 60:1033-1037,1994.
Fanner, Int J Syst Bacteriol, 43: 232-236, 1993.
Tirado-Acevedo, Production of Bioethanol from Synthesis Gas Using Clostridium Ijungdahlii, PhD thesis, North Carolina State University, 2010.
Wang, J Bacteriol, 195: 4373-4386, 2013.
Williams, J Gen Microbiol, 136: 819-826, 1990.
Wolfe, Adv Microbiol Physiol, 6:107-146, 1971.
Diekert et al. J. Bacerol 1978, pp. 597-606.
Jung et al. APPLD Microbiol and Biotech 2012,95, pp. 461-469.
Muller App env microbial 2003, p. 63445-6353.
Tracy et al. (Cur op biotechnol. 2011, 364-381).
Supplementary European Search Report for Patent Application EP15742928, European Patent Office, Aug. 22, 2017, 11 pages.
Durre, Species and Strain Identification Methods, Handbook on Clostridia, edited by Peter Durre, CRC press, p. 4, 2005.
Hu, Anaerobic C02 Fixation by the Acetogenic Bacterium Moorella thermoacetica, AIChE Journal, 59: 3176-3183, 2013.
Li, Combined inactivation of the Clostridium cellulolyticum lactate and malate dehydrogenase genes substantially ncreases ethanol yield from cellulose and switchgrass fermentations, Biotechnol Biofuels, 5:2, 2012.

* cited by examiner

SEQUENCE LISTING

```
<160> NUMBER OF SEQ ID NOS: 12

<210> SEQ ID NO 1
<211> LENGTH: 1000
<212> TYPE: DNA
<213> ORGANISM: Artificial sequence
<220> FEATURE:
<223> OTHER INFORMATION: Synthetic

<400> SEQUENCE: 1
tggtattcta gcttgaaatt tgaacttata catgaaatat aatgacaaaa ttgaaatcac      60
atttaaaaac ttttttaaat aagtcttagc ttggtatttt agaaaacctt aggaacttag     120
atatgtttga ggtacgagtt gatctaagtt cctttaggtt ttcaaaatac caagctttag     180
acttattaaa agtttttata gtgatgaaat ttgtcattat atgatattgt ataagtgaac     240
tttcaaccta gaaatatcta aatgtctaaa attatatctt ctaaacttct ttttggtaca     300
tgatggactt tattctcgtc tctccagtac ttcacatcat tatttgaatc catagcttct     360
```

```
ataaccactt gttcctttgg ctttccaaga gctactacca atataatttc atatttttca    420
tccaaattaa gatttgattt taattctttt ttattcacat ttcccagcat acatccgcca    480
aatccttttt ctacagctcc tagtaaaata gtttgagctg ctattccagg atcaaatgat    540
gggcttttac taatagatgt gtcattaagt ataacaacaa aaccacttgg tttttcacct    600
tcttcaggtc catcccagtc ctttaaatat cctgcccaac ccaaagtctt aaatattttt    660
tcattattat cttctgtatt tgatataaca tattttagtg gctgcaaatt tgaacctgat    720
gctgataatc tggcaaggtt caccaaatat tttaaagttt ccacagttat ttttcattc     780 tgatagaatc ttctacagga tctatttttt aaaactagtt cttttatcat attcatccct    840
ccaagctaat aacttaatat cattacaatt atcatatctc taaacaaatt gaatatcaat    900
caaatatagt aaatataaag gtaatattga attatatata atgttactat aaaattatat    960
atagtaaata ttattcataa aaaggggggag ctagaataca                          1000

<210> SEQ ID NO 2
<211> LENGTH: 1000
<212> TYPE: DNA
<213> ORGANISM: Artificial sequence
<220> FEATURE:
<223> OTHER INFORMATION: Synthetic

<400> SEQUENCE: 2
acaaaagttc ttatgcactc ttcttttttt gataaaagaa gagtgcattg atttttaatgt    60 tttttatct tatttataga atatagaaat cttagcaact agacttaaac cataatcaag     120
ttaaaatctt ggtaaatcct ttaaattttc aacatccata acatcagggt cagctactaa    180
atattctcct ccatctttac ctttaaatac gccaactcct tcaattatgt gctcccttgc    240
catcattata gcatgattta aggaagcac ctcaccattt tcaagtaata catctgtaat    300
cttaccctca tgatctttcc ttactttaat tattttttgaa ttttttcatta tatacctcct    360 gattagatat atcattaata tatattttga gagaaaactc aactacttat acaaaatatt    420
tttacattat atttacacaa ttataacttt tgtggttgca attaaagtta taattgaacc    480
aaatcttgtt attgacagta caaaatgcaa gtcatatatt tatccgatga ctacccgctc    540
taatactttc cctcttttcc aagtgggagt aaagagcgga tacgtccctg gataacgatt    600
tttcctaaag gataacgcct tctaagtgct gaagcactaa gaatcctgtt aataagcatc    660
aggtggagtt aaacctccat ctgatactaa gaactctgtt tataacatga tttgcaaata    720
tatcactttg gaggaatttt atgaaaaaaa atattattaa aagttccata gtatttatgg    780 tgattttttgc tttatttttt atagcatcag ataaatcaac tgttcatgca ttaaattgct    840
atacagtaag cttgtcaaat tttaaagagg tatcccaaaa catttatgta cagccaaata    900
cttctgataa agatataaat aatatattga gtaccatttc caaatctaaa aacattgtgg    960
ccaatttata tggaagtttc aatgctaaac ctgtctttat                           1000

<210> SEQ ID NO 3
<211> LENGTH: 4746
<212> TYPE: DNA
<213> ORGANISM: Artificial sequence
<220> FEATURE:
<223> OTHER INFORMATION: Synthetic

<400> SEQUENCE: 3
cctgcaggtt aagagcaaca ctgtacgtgg tattctagct tgaaatttga acttatacat     60
```

```
gaaatataat gacaaaattg aaatcacatt taaaaacttt tttaaataag tcttagcttg    120
gtattttaga aaaccttagg aacttagata tgtttgaggt acgagttgat ctaagttcct    180
ttaggttttc aaaataccaa gctttagact tattaaaagt ttttatagtg atgaaatttg    240
tcattatatg atattgtata agtgaacttt caacctagaa atatctaaat gtctaaaatt    300
atatcttcta aacttctttt tggtacatga tggactttat tctcgtctct ccagtacttc    360
acatcattat ttgaatccat agcttctata accacttgtt cctttggctt tccaagagct    420
actaccaata taatttcata tttttcatcc aaattaagat ttgattttaa ttctttttta    480
ttcacatttc ccagcataca tccgccaaat cctttttcta cagctcctag taaaatagtt    540
tgagctgcta ttccaggatc aaatgatggg cttttactaa tagatgtgtc attaagtata    600
acaacataac cacttggttt ttcaccttct tcaggtccat cccagtcctt taaatatcct    660
gcccaaccca aagtcttaaa tattttttca ttattatctt ctgtatttga tataacatat    720
tttagtggct gcaaatttga acctgatgct gataatctgg caaggttcac caaatatttt    780
aaagtttcca cagttatttt ttcattctga tagaatcttc tacaggatct atttttttaaa    840 actagttctt ttatcatatt catccctcca agctaataac ttaatatcat tacaattatc    900
atatctctaa acaaattgaa tatcaatcaa atatagtaaa tataaaggta atattgaatt    960
atatataatg ttactataaa attatatata gtaaatatta ttcataaaaa gggggagcta   1020
gaatacaatg aaagtgctag cgaaggcaaa gaaaatccat ggcaaattga ataaacaaaa   1080
gttcttatgc actcttcttt ttttgataaa agaagagtgc attgatttta atgttttttt   1140
atcttattta tagaatatag aaatcttagc aactagactt aaaccataat caagttaaaa   1200
tcttggtaaa tcctttaaat tttcaacatc cataacatca gggtcagcta ctaaatattc   1260
tcctccatct ttacctttaa atacgccaac tccttcaatt atgtgctccc ttgccatcat   1320
tatagcatga tttaaaggaa gcacctcacc attttcaagt aatacatctg taatcttacc   1380
ctcatgatct ttccttactt taattatttt tgaattttc attatatacc tcctgattag    1440
atatatcatt aatatatatt ttgagagaaa actcaactac ttatacaaaa tattttttaca   1500 ttatatttac acaattataa cttttgtggt tgcaattaaa gttataattg aaccaaatct   1560
tgttattgac agtacaaaat gcaagtcata tatttatccg atgactaccc gctctaatac   1620
tttccctctt ttccaagtgg gagtaaagag cggatacgtc cctggataac gattttcct    1680 aaaggataac gccttctaag tgctgaagca ctaagaatcc tgttaataag catcaggtgg   1740
agttaaacct ccatctgata ctaagaactc tgttttataac atgatttgca aatatatcac   1800
tttggaggaa ttttatgaaa aaaatatatta ttaaaagttc catagtattt atggtgatt    1860 ttgctttatt ttttatagca tcagataaat caactgttca tgcattaaat tgctatacag   1920
taagcttgtc aaattttaaa gaggtatccc aaaacattta tgtacagcca aatacttctg   1980
ataaagatat aaataatata ttgagtacca tttccaaatc taaaaacatt gtggccaatt   2040
tatatgaaag tttcaatgct aaacctgtct ttataattag caaagattca acagccttaa   2100
aaaaatttgg tgttgaaaat aaaacaggag ctacacaaaa aactatacta ggtagctaca   2160
tagttctggg accagaggga ttaaatcggc gcgccgcatt cacttctttt ctatataaat   2220
atgagcgaag cgaataagcg tcggaaaagc agcaaaaagt ttccttttttg ctgttggagc   2280 atggggggttc aggggggtgca gtatctgacg tcaatgccga gcgaaagcga gccgaagggt   2340
agcatttacg ttagataacc ccctgatatg ctccgacgct ttatatagaa aagaagattc   2400
aactaggtaa aatcttaata taggttgaga tgataaggtt tataaggaat tgtttgttc    2460
```

```
taattttttca ctcatttttgt tctaatttct tttaacaaat gttcttttt ttttagaaca    2520 gttatgatat agttagaata gtttaaaata aggagtgaga aaaagatgaa agaaagatat    2580
ggaacagtct ataaaggctc tcagaggctc atagacgaag aaagtggaga agtcatagag    2640
gtagacaagt tataccgtaa acaaacgtct ggtaacttcg taaaggcata tatagtgcaa    2700
ttaataagta tgttagatat gattggcgga aaaaaactta aaatcgttaa ctatatccta    2760
gataatgtcc acttaagtaa caatacaatg atagctacaa caagagaaat agcaaaagct    2820
acaggaacaa gtctacaaac agtaataaca acacttaaaa tcttagaaga aggaaatatt    2880
ataaaaagaa aaactggagt attaatgtta aaccctgaac tactaatgag aggcgacgac    2940
caaaaacaaa aatacctctt actcgaattt gggaactttg agcaagaggc aaatgaaata    3000
gattgacctc ccaataacac cacgtagtta ttgggaggtc aatctatgaa atgcgattaa    3060
gggccggcca gtgggcaagt tgaaaaattc acaaaaatgt ggtataatat ctttgttcat    3120
tagagcgata aacttgaatt tgagagggaa cttagatggt atttgaaaaa attgataaaa    3180
atagttggaa cagaaaagag tattttgacc actactttgc aagtgtacct tgtacctaca    3240
gcatgaccgt taaagtggat atcacacaaa taaggaaaa gggaatgaaa ctatatcctg     3300 caatgctta ttatattgca atgattgtaa accgccattc agagtttagg acggcaatca     3360
atcaagatgg tgaattgggg atatatgatg agatgatacc aagctataca atatttcaca    3420
atgatactga aacattttcc agcctttgga ctgagtgtaa gtctgacttt aaatcatttt    3480
tagcagatta tgaaagtgat acgcaacggt atggaaacaa tcatagaatg gaaggaaagc    3540
caaatgctcc ggaaaacatt tttaatgtat ctatgatacc gtggtcaacc ttcgatggct    3600
ttaatctgaa tttgcagaaa ggatatgatt atttgattcc tattttact atggggaaat     3660 attataaaga agataacaaa attatacttc ctttggcaat tcaagttcat cacgcagtat    3720
gtgacggatt tcacatttgc cgtttttgtaa acgaattgca ggaattgata atagttaac     3780 ttcaggtttg tctgtaacta aaaacaagta tttaagcaaa aacatcgtag aaatacggtg    3840 tttttttgtta ccctaagttt aaactccttt ttgataatct catgaccaaa atcccttaac   3900
gtgagttttc gttccactga gcgtcagacc ccgtagaaaa gatcaaagga tcttcttgag    3960 atccttttttt tctgcgcgta atctgctgct tgcaaacaaa aaaaccaccg ctaccagcgg   4020
tggtttgttt gccggatcaa gagctaccaa ctcttttttcc gaaggtaact ggcttcagca   4080
gagcgcagat accaaatact gttcttctag tgtagccgta gttaggccac cacttcaaga    4140
actctgtagc accgcctaca tacctcgctc tgctaatcct gttaccagtg ctgctgccca    4200
gtggcgataa gtcgtgtctt accgggttgg actcaagacg atagttaccg gataaggcgc    4260
agcggtcggg ctgaacgggg ggttcgtgca cacagcccag cttggagcga acgacctaca    4320
ccgaactgag atacctacag cgtgagctat gagaaagcgc cacgcttccc gaagggagaa    4380
aggcggacag gtatccggta agcggcaggg tcggaacagg agagcgcacg agggagcttc    4440 caggggggaaa cgcctggtat ctttatagtc ctgtcgggtt tcgccacctc tgacttgagc    4500
gtcgattttt gtgatgctcg tcagggggc ggagcctatg gaaaaacgcc agcaacgcgg     4560 ccttttttacg gttcctggcc ttttgctggc cttttgctca catgttcttt cctgcgttat    4620
cccctgattc tgtggataac cgtattaccg cctttgagtg agctgatacc gctcgccgca    4680
gccgaacgac cgagcgcagc gagtcagtga gcgaggaagc ggaagagcgc ccaatacgca    4740
gggccc                                                              4746
```

<210> SEQ ID NO 4
<211> LENGTH: 39
<212> TYPE: DNA
<213> ORGANISM: Artificial sequence
<220> FEATURE:
<223> OTHER INFORMATION: Synthetic

<400> SEQUENCE: 4
attcatcctg caggttaaga gcaacactgt acgtggtat                        39

<210> SEQ ID NO 5
<211> LENGTH: 37
<212> TYPE: DNA
<213> ORGANISM: Artificial sequence
<220> FEATURE:
<223> OTHER INFORMATION: Synthetic

<400> SEQUENCE: 5
gactggcgcg ccatttaatc cctctggtcc cagaact                          37

<210> SEQ ID NO 6
<211> LENGTH: 25
<212> TYPE: DNA
<213> ORGANISM: Artificial sequence
<220> FEATURE:
<223> OTHER INFORMATION: Synthetic

<400> SEQUENCE: 6
tgaactaaaa agtttcgtac gatgt                                       25

<210> SEQ ID NO 7
<211> LENGTH: 25
<212> TYPE: DNA
<213> ORGANISM: Artificial sequence
<220> FEATURE:
<223> OTHER INFORMATION: Synthetic

<400> SEQUENCE: 7
tcctttatcc attgtccctc agagt                                       25

<210> SEQ ID NO 8
<211> LENGTH: 309
<212> TYPE: DNA
<213> ORGANISM: Artificial sequence
<220> FEATURE:
<223> OTHER INFORMATION: Synthetic

<400> SEQUENCE: 8
ttatccttag acttcgccaa ggtgcgccca gatagggtgt taagtcaagt agtttaaggt    60
actactctgt aagataacac agaaaacagc caacctaacc gaaagcgaa agctgatacg    120 ggaacagagc acggttggaa agcgatgagt tacctaaaga caatcgggta cgactgagtc   180
gcaatgttaa tcagatataa ggtataagtt gtgtttactg aacgcaagtt tctaatttcg   240
attaagtctc gatagaggaa agtgtctgaa acctctagta caaagaaagg taagttaccc   300
ttggcgact                                                          309

<210> SEQ ID NO 9
<211> LENGTH: 45
<212> TYPE: DNA
<213> ORGANISM: Artificial sequence
<220> FEATURE:
<223> OTHER INFORMATION: Synthetic

<400> SEQUENCE: 9
ccaactatgg aaaatgcaga cttggccaag ggatttgact gcatc 45

<210> SEQ ID NO 10
<211> LENGTH: 37
<212> TYPE: DNA
<213> ORGANISM: Artificial sequence
<220> FEATURE:
<223> OTHER INFORMATION: Synthetic

<400> SEQUENCE: 10
ccgaattcgt cgacaacaga gtttgatcct ggctcag 37

<210> SEQ ID NO 11
<211> LENGTH: 37
<212> TYPE: DNA
<213> ORGANISM: Artificial sequence
<220> FEATURE:
<223> OTHER INFORMATION: Synthetic

<400> SEQUENCE: 11
cccgggatcc aagcttacgg ctaccttgtt acgactt 37

<210> SEQ ID NO 12
<211> LENGTH: 9034
<212> TYPE: DNA
<213> ORGANISM: Artificial sequence
<220> FEATURE:
<223> OTHER INFORMATION: Synthetic

<400> SEQUENCE: 12

| | | |
|---|---|---|
| agaaggccat cctgacggat ggcctttttg cgtttctaca aactcttcct gtcgtcatat | 60 |
| ctacaagcca tcccccacaca gatacgggcg cgccgccatt attttttga acaattgaca | 120 |
| attcatttct tatttttat taagtgatag tcaaaaggca taacagtgct gaatagaaag | 180 |
| aaatttacag aaaagaaaat tatagaattt agtatgatta attatactca tttatgaatg | 240 |
| tttaattgaa tacaaaaaaa aatacttgtt atgtattcaa ttacgggtta aaatatagac | 300 |
| aagttgaaaa atttaataaa aaaataagtc ctcagctctt atatattaag ctaccaactt | 360 |
| agtatataag ccaaaactta aatgtgctac caacacatca agccgttaga gaactctatc | 420 |
| tatagcaata tttcaaatgt accgacatac aagagaaaca ttaactatat atattcaatt | 480 |
| tatgagatta tcttaacaga tataaatgta aattgcaata agtaagattt agaagtttat | 540 |
| agcctttgtg tattggaagc agtacgcaaa ggctttttta tttgataaaa attagaagta | 600 |
| tatttatttt tcataatta atttatgaaa atgaaagggg gtgagcaaag tgacagagga | 660 |
| aagcagtatc ttatcaaata acaaggtatt agcaatatca ttattgactt agcagtaaaa | 720 |
| cattatgact tttatagtgc ttgtagctaa gtagtacgaa agggggagct ttaaaaagct | 780 |
| ccttggaata catagaattc ataaattaat ttatgaaaag aagggcgtat atgaaaactt | 840 |
| gtaaaaattg caaagagttt attaaagata ctgaaatatg caaatacat tcgttgatga | 900 |
| ttcatgataa aacagtagca acctattgca gtaaatacaa tgagtcaaga tgtttacata | 960 |
| aagggaaagt ccaatgtatt aattgttcaa agatgaaccg atatggatgg tgtgccataa | 1020 |
| aaatgagatg ttttacagag gaagaacaga aaaagaacg tacatgcatt aaatattatg | 1080 |
| caaggagctt taaaaaagct catgtaaaga agagtaaaaa gaaaaaataa tttatttatt | 1140 |
| aatttaatat tgagagtgcc gacacagtat gcactaaaaa atatatctgt ggtgtagtga | 1200 |
| gccgatacaa aaggatagtc actcgcattt tcataataca tcttatgtta tgattatgtg | 1260 |

```
tcggtgggac ttcacgacga aaacccacaa taaaaaaaga gttcggggta gggttaagca    1320
tagttgaggc aactaaacaa tcaagctagg atatgcagta gcagaccgta aggtcgttgt    1380
ttaggtgtgt tgtaatacat acgctattaa gatgtaaaaa tacggatacc aatgaaggga    1440
aaagtataat ttttggatgt agtttgtttg ttcatctatg ggcaaactac gtccaaagcc    1500
gtttccaaat ctgctaaaaa gtatatcctt tctaaaatca aagtcaagta tgaaatcata    1560
aataaagttt aattttgaag ttattatgat attatgtttt tctattaaaa taaattaagt    1620
atatagaata gtttaataat agtatatact taatgtgata agtgtctgac agtgtcacag    1680
aaaggatgat tgttatggat tataagcggc cggccagtgg gcaagttgaa aaattcacaa    1740
aaatgtggta taatatcttt gttcattaga gcgataaact tgaatttgag agggaactta    1800
gatggtattt gaaaaaattg ataaaaatag ttggaacaga aaagagtatt ttgaccacta    1860 cttttgcaagt gtaccttgta cctacagcat gaccgttaaa gtggatatca cacaaataaa    1920
ggaaaaggga atgaaactat atcctgcaat gctttattat attgcaatga ttgtaaaccg    1980
ccattcagag tttaggacgg caatcaatca agatggtgaa ttgggatat atgatgagat    2040 gataccaagc tatacaatat ttcacaatga tactgaaaca ttttccagcc tttggactga    2100
gtgtaagtct gactttaaat cattttttagc agattatgaa agtgatacgc aacggtatgg    2160
aaacaatcat agaatggaag gaaagccaaa tgctccggaa aacattttta atgtatctat    2220
gataccgtgg tcaaccttcg atggctttaa tctgaatttg cagaaaggat atgattattt    2280
gattcctatt tttactatgg ggaaatatta taaagaagat aacaaaatta tacttccttt    2340
ggcaattcaa gttcatcacg cagtatgtga cggatttcac atttgccgtt ttgtaaacga    2400
attgcaggaa ttgataaata gttaacttca ggtttgtctg taactaaaaa caagtattta    2460
agcaaaaaca tcgtagaaat acggtgtttt ttgttaccct aagtttaaac tccttttga    2520 taatctcatg accaaaatcc cttaacgtga gttttcgttc cactgagcgt cagaccccgt    2580
agaaaagatc aaaggatctt cttgagatcc ttttttttctg cgcgtaatct gctgcttgca    2640
aacaaaaaaa ccaccgctac cagcggtggt ttgtttgccg gatcaagagc taccaactct    2700 tttttccgaag gtaactggct tcagcagagc gcagatacca aatactgtcc ttctagtgta    2760
gccgtagtta ggccaccact tcaagaactc tgtagcaccg cctacatacc tcgctctgct    2820
aatcctgtta ccagtggctg ctgccagtgg cgataagtcg tgtcttaccg ggttggactc    2880
aagacgatag ttaccggata aggcgcagcg gtcgggctga acggggggtt cgtgcacaca    2940
gcccagcttg gagcgaacga cctacaccga actgagatac ctacagcgtg agcattgaga    3000
aagcgccacg cttcccgaag ggagaaaggc ggacaggtat ccggtaagcg gcagggtcgg    3060
aacaggagag cgcacgaggg agcttccagg gggaaacgcc tggtatcttt atagtcctgt    3120
cgggtttcgc cacctctgac ttgagcgtcg attttttgtga tgctcgtcag ggggcggag    3180 cctatggaaa aacgccagca acgcggcctt tttacggttc ctggcctttt gctggccttt    3240
tgctcacatg ttctttcctg cgttatcccc tgattctgtg gataaccgta ttaccgcctt    3300
tgagtgagct gataccgctc gccgcagccg aacgaccgag cgcagcgagt cagtgagcga    3360
ggaagcggaa gagcgcccaa tacgcagggc cccctgcttc ggggtcatta tagcgatttt    3420
ttcggtatat ccatcctttt tcgcacgata tacaggattt tgccaaaggg ttcgtgtaga    3480
ctttccttgg tgtatccaac ggcgtcagcc gggcaggata ggtgaagtag gcccacccgc    3540
gagcgggtgt tccttcttca ctgtccctta ttcgcacctg gcggtgctca acgggaatcc    3600
tgctctgcga ggctggccgg ctaccgccgg cgtaacagat gagggcaagc ggatggctga    3660
```

```
tgaaaccaag ccaaccagga agggcagccc acctatcaag gtgtactgcc ttccagacga   3720
acgaagagcg attgaggaaa aggcggcggc ggccggcatg agcctgtcgg cctacctgct   3780
ggccgtcggc cagggctaca aaatcacggg cgtcgtggac tatgagcacg tccgcgagct   3840
ggcccgcatc aatggcgacc tgggccgcct gggcggcctg ctgaaactct ggctcaccga   3900
cgacccgcgc acggcgcggt tcggtgatgc cacgatcctc gccctgctgg cgaagatcga   3960
agagaagcag gacgagcttg gcaaggtcat gatgggcgtg gtccgcccga gggcagagcc   4020 atgactttt tagccgctaa aacggccggg gggtgcgcgt gattgccaag cacgtcccca   4080
tgcgctccat caagaagagc gacttcgcgg agctggtgaa gtacatcacc gacgagcaag   4140
gcaagaccga tcgggccccc tgcagggtgt agtagcctgt gaataagta aggaaaaaaa   4200 agaagtaagt gttatatatg atgattattt tgtagatgta gataggataa tagaatccat   4260
agaaaatata ggttatacag ttatataaaa attactttaa aaattaataa aaacatggta   4320
aaatataaat cgtataaagt tgtgtaattt ttaagcttta taattatcct tagacttcgc   4380
caaggtgcgc ccagataggg tgttaagtca agtagtttaa ggtactactc tgtaagataa   4440
cacagaaaac agccaaccta accgaaaagc gaaagctgat acgggaacag agcacggttg   4500
gaaagcgatg agttacctaa agacaatcgg gtacgactga gtcgcaatgt taatcagata   4560
taaggtataa gttgtgttta ctgaacgcaa gtttctaatt tcgattaagt ctcgatagag   4620
gaaagtgtct gaaacctcta gtacaaagaa aggtaagtta cccttggcga cttatctgtt   4680
atcaccacat ttgtacaatc tgtaggagaa cctatgggaa cgaaacgaaa gcgatgccga   4740
gaatctgaat ttaccaagac ttaacactaa ctggggatac cctaaacaag aatgcctaat   4800
agaaaggagg aaaaaggcta tagcactaga gcttgaaaat cttgcaaggg tacggagtac   4860
tcgtagtagt ctgagaaggg taacgccctt tacatggcaa aggggtacag ttattgtgta   4920
ctaaaattaa aaattgatta gggaggaaaa cctcaaaatg aaaccaacaa tggcaatttt   4980
agaaagaatc agtaaaaatt cacaagaaaa tatagacgaa gttttacaa gactttatcg   5040 ttatcttta cgtccagata tttattacgt ggcgacgcgt gaagttccta tactttctag   5100
agaataggaa cttcgcgact catagaatta tttcctcccg ttaaataata gataactatt   5160
aaaaatagac aatacttgct cataagtaac ggtacttaaa ttgtttactt ggcgtgttt   5220 cattgcttga tgaaactgat ttttagtaaa cagttgacga tattctcgat tgacccattt   5280
tgaaacaaag tacgtatata gcttccaata tttatctgga acatctgtgg tatggcgggt   5340
aagttttatt aagacactgt ttacttttgg tttaggatga aagcattccg ctggcagctt   5400
aagcaattgc tgaatcgaga cttgagtgtg caagagcaac cctagtgttc ggtgaatatc   5460
caaggtacgc ttgtagaatc cttcttcaac aatcagatag atgtcagacg catggctttc   5520
aaaaaccact ttttaataa tttgtgtgct taaatggtaa ggaatactcc caacaatttt   5580
atacctctgt ttgttaggga attgaaactg tagaatatct tggtgaatta aagtgacacg   5640
agtattcagt tttaattttt ctgacgataa gttgaataga tgactgtcta attcaataga   5700
cgttacctgt ttacttattt tagccagttt cgtcgttaaa tgcccttac ctgttccaat   5760 ttcgtaaacg gtatcggttt cttttaaatt caattgtttt attatttggt tgagtacttt   5820
ttcactcgtt aaaaagtttt gagaatattt tatattttg ttcataccag caccagaagc   5880
accagcatct cttgggttaa ttgaggcctg agtataaggt gacttatact tgtaatctat   5940
ctaaacgggg aacctctcta gtagacaatc ccgtgctaaa ttgtaggact gcccttaat   6000
```

```
aaatacttct atatttaaag aggtatttat gaaaagcgga atttatcaga ttaaaaatac    6060
tttctctaga gaaaatttcg tctggattag ttacttatcg tgtaaaatct gataaatgga    6120
attggttcta cataaatgcc taacgactat ccctttgggg agtagggtca agtgactcga    6180
aacgatagac aacttgcttt aacaagttgg agatatagtc tgctctgcat ggtgacatgc    6240
agctggatat aattccgggg taagattaac gaccttatct gaacataatg ccatatgaat    6300
ccctcctaat ttatacgttt tctctaacaa cttaattata cccactatta ttattttat     6360 caatatagaa gttcctatac tttctagaga ataggaactt cacgcgttgg gaaatggcaa    6420
tgatagcgaa acaacgtaaa actcttgttg tatgctttca ttgtcatcgt cacgtgattc    6480
ataaacacaa gtgaatgtcg acagtgaatt tttacgaacg aacaataaca gagccgtata    6540
ctccgagagg ggtacgtacg gttcccgaag agggtggtgc aaaccagtca cagtaatgtg    6600
aacaaggcgg tacctcccta cttcaccata tcattttctg cagcccccta gaaataattt    6660
tgtttaactt taagaaggag atatacatat atggctagat cgtccattcc gacagcatcg    6720
ccagtcacta tggcgtgctg ctagcgctat atgcgttgat gcaatttcta tgcactcgta    6780
gtagtctgag aagggtaacg ccctttacat ggcaaagggg tacagttatt gtgtactaaa    6840
attaaaaatt gattagggag gaaaacctca aaatgaaacc aacaatggca attttagaaa    6900
gaatcagtaa aaattcacaa gaaaatatag acgaagtttt tacaagactt tatcgttatc    6960
ttttacgtcc agatatttat tacgtggcgt atcaaaattt atattccaat aaaggagctt    7020
ccacaaaagg aatattagat gatacagcgg atggctttag tgaagaaaaa ataaaaaaga    7080
ttattcaatc tttaaaagac ggaacttact atcctcaacc tgtacgaaga atgtatattg    7140
caaaaaagaa ttctaaaaag atgagacctt taggaattcc aactttcaca gataaattga    7200
tccaagaagc tgtgagaata attcttgaat ctatctatga accggtattc gaagatgtgt    7260
ctcacggttt tagacctcaa cgaagctgtc acacagcttt gaaaacaatc aaaagagagt    7320
ttggcggcgc aagatggttt gtggagggag atataaaagg ctgcttcgat aatatagacc    7380
acgttacact cattggactc atcaatctta aaatcaaaga tatgaaaatg agccaattga    7440
tttataaatt tctaaaagca ggttatctgg aaaactggca gtatcacaaa acttacagcg    7500
gaacacctca aggtggaatt ctatctcctc ttttggccaa catctatctt catgaattgg    7560
ataagtttgt tttacaactc aaaatgaagt ttgaccgaga aagtccagaa agaataacac    7620
ctgaatatcg ggagctccac aatgagataa aaagaatttc tcaccgtctc aagaagttgg    7680
agggtgaaga aaaagctaaa gttcttttag aatatcaaga aaaacgtaaa agattaccca    7740
cactcccctg tacctcacag acaaataaag tattgaaata cgtccggtat gcggacgact    7800
tcattatctc tgttaaagga agcaaagagg actgtcaatg gataaagaa caattaaaac      7860 ttttattca taacaagcta aaaatggaat tgagtgaaga aaaaacactc atcacacata    7920
gcagtcaacc cgctcgtttt ctgggatatg atatacgagt aaggagatct ggaacgataa    7980
aacgatctgg taaagtcaaa aagagaacac tcaatgggag tgtagaactc cttattcctc    8040
ttcaagacaa aattcgtcaa tttattttg acaagaaaat agctatccaa aagaaagata    8100
gctcatggtt tccagttcac aggaaatatc ttattcgttc aacagactta gaaatcatca    8160
caatttataa ttctgaactc cgcgggattt gtaattacta cggtctagca agtaatttta    8220
accagctcaa ttattttgct tatcttatgg aatacagctg tctaaaaacg atagcctcca    8280
aacataaggg aacactttca aaaaccattt ccatgtttaa agatggaagt ggttcgtggg    8340
ggatcccgta tgagataaag caaggtaagc agcgccgtta ttttgcaaat tttagtgaat    8400
```

```
gtaaatcccc ttatcaattt acggatgaga taagtcaagc tcctgtattg tatggctatg    8460
cccggaatac tcttgaaaac aggttaaaag ctaaatgttg tgaattatgt gggacgtctg    8520
atgaaaatac ttcctatgaa attcaccatg tcaataaggt caaaaatctt aaaggcaaag    8580
aaaaatggga aatggcaatg atagcgaaac aacgtaaaac tcttgttgta tgctttcatt    8640
gtcatcgtca cgtgattcat aaacacaagt gaatgtcgag cacccgttct cggagcactg    8700
tccgaccgct ttggccgccg cccagtcctg ctcgcttcgc tacttggagc cactatcgac    8760
tacgcgatca tggcgaccac acccgtcctg tggatcgcca agccgccgat ggtagtgtgg    8820
ggtctcccca tgcgagagta gggaactgcc aggcatcaaa taaaacgaaa ggctcagtcg    8880
aaagactggg cctttcgttt tatctgttgt ttgtcggtga acgctctcct gagtaggaca    8940
aatccgccgg gagcggattt gaacgttgcg aagcaacggc ccggagggtg gcgggcagga    9000
cgcccgccat aaactgccag gcatcaaatt aagc                                9034
```

RECOMBINANT MICROORGANISMS AND METHODS OF USE THEREOF

CROSS REFERENCE TO RELATED APPLICATIONS

This application is a divisional of U.S. patent application Ser. No. 14/609,420 filed Jan. 29, 2015 which claims the benefit of U.S. Provisional Patent Application 61/933,815 filed Jan. 30, 2014 and U.S. Provisional Patent Application 61/944,541 filed Feb. 25, 2014, the entirety of which are incorporated herein by reference.

BACKGROUND OF THE INVENTION

An acetogen is a microorganism that generates or is capable of generating acetate as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate and ethanol (Ragsdale, *Biochim Biophys Acta*, 1784: 1873-1898, 2008).

Many acetogens naturally produce at least two or more products. However, this is not necessarily desirable on a commercial scale, since the production of multiple products is detrimental to the efficiency and yield of each individual product. In particular, byproducts may divert carbon away from the biosynthetic pathways of a target product, introduce toxicity concerns, impede the recovery and separation of a target product, complicate the control of fermentation conditions favoring a target product, and serve as a substrate for contaminating microorganisms.

For instance, acetogens such as *Clostridium autoethanogenum*, *Clostridium ljungdahlii*, *Clostridium ragsdalei* (Köpke, *Appl Environ Microbiol*, 77: 5467-5475, 2011), and *Butyribacterium methylotrophicum* (Heiskanen, *Enzyme Microb Technol*, 41 362-367, 2007) may produce lactate as a byproduct. This production of lactate reduces the efficiency and yield of target products, such as ethanol, butanol, or 2,3-butanediol. Additionally, lactate may be toxic to acetogens such as *Clostridium autoethanogenum* even at low concentrations (Köpke, *Appl Environ Microbiol*, 77: 5467-5475, 2011) and may serve as a substrate for other bacteria, increasingly the likelihood of bacterial contamination when lactate is produced. Furthermore, separating lactate from other products, such as ethanol, may require cumbersome processing steps.

Accordingly, there is a strong need for microorganisms and methods that reduce or eliminate the production of byproducts, such as lactate.

SUMMARY OF THE INVENTION

The invention provides a carboxydotrophic acetogenic bacterium comprising a disrupting mutation in a lactate biosynthesis pathway enzyme. In one embodiment, the disrupting mutation reduces or eliminates the expression or activity of the lactate biosynthesis pathway enzyme.

The disrupting mutation affects the ability of the bacterium to produce lactate. In one embodiment, the bacterium of the invention produces a reduced amount of lactate compared to a parental bacterium. In one embodiment, the bacterium of the invention produces substantially no lactate.

The bacterium of the invention may produce products, such as one or more of ethanol, 2,3-butanediol, formate, pyruvate, succinate, valine, leucine, isoleucine, malate, fumarate, 2-oxogluterate, citrate, and citramalate. In one embodiment, the bacterium of the invention produces an increased amount of one or more of ethanol, 2,3-butanediol, formate, pyruvate, succinate, valine, leucine, isoleucine, malate, fumarate, 2-oxogluterate, citrate, and citramalate compared to a parental bacterium.

In one embodiment, the lactate biosynthesis pathway enzyme is an enzyme that natively converts pyruvate to lactate. In a preferred embodiment, the lactate biosynthesis pathway enzyme is lactate dehydrogenase (LDH).

The bacterium of the invention may be derived from a parental bacterium, such as *Clostridium autoethanogenum*, *Clostridium ljungdahlii*, and *Clostridium ragsdalei*. In a preferred embodiment, the parental bacterium is *Clostridium autoethanogenum* deposited under DSMZ accession number DSM23693.

The invention further provides a method of producing a product comprising culturing the bacterium of the invention in the presence of a substrate comprising CO whereby the bacterium produces a product.

DETAILED DESCRIPTION OF THE INVENTION

Figure 1:
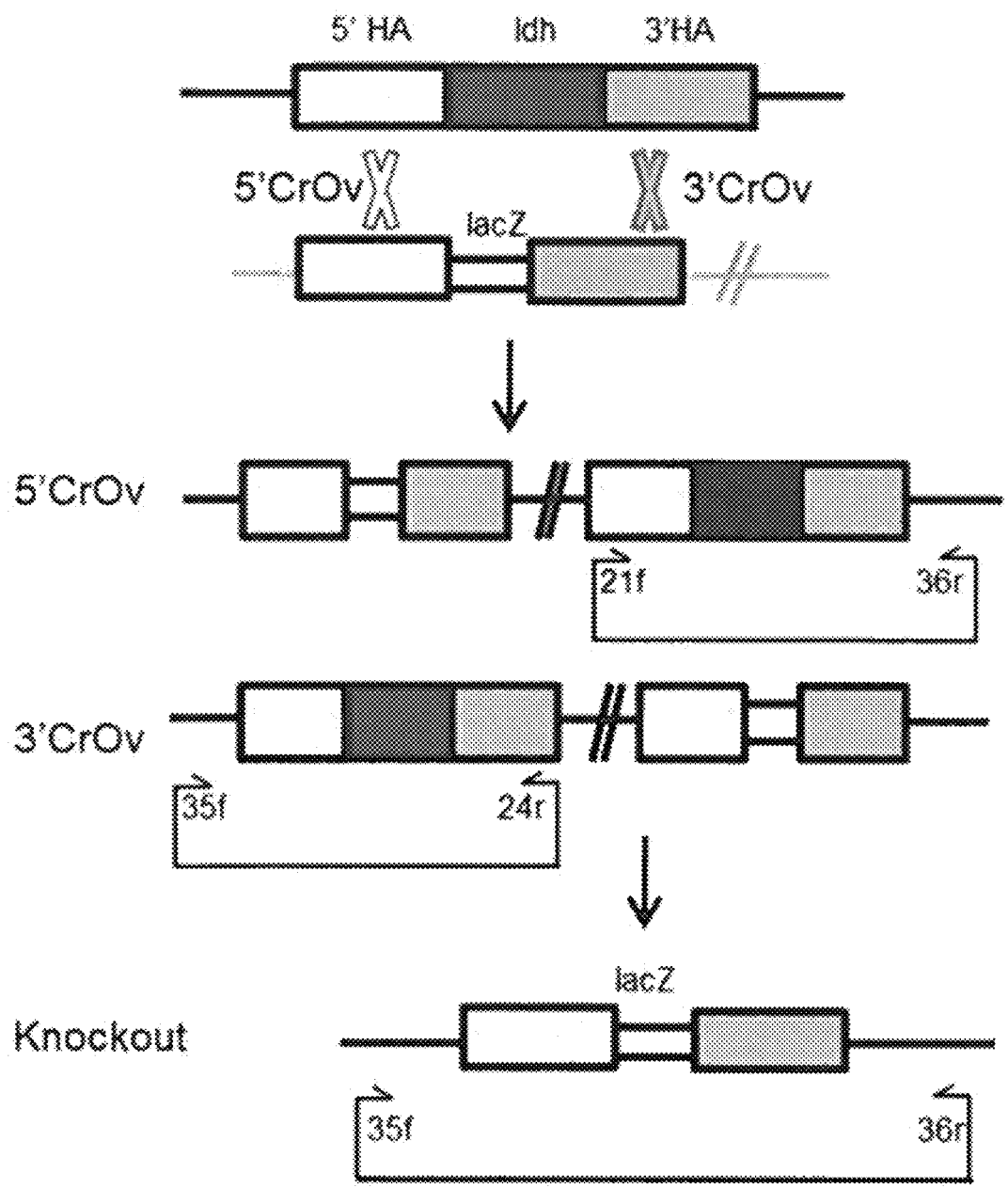
FIG. 1 is a diagram showing a LDH knockout strategy and the primers used for screening.

The inventors have discovered that disruption of the lactate biosynthesis pathway in an acetogenic bacterium results in increased or more efficient production of products, such as ethanol, 2,3-butanediol, formate, succinate, 2-oxogluterate, valine, leucine, and isoleucine, compared to a parental microorganism, and may also result in increased or more efficient production of pyruvate, malate, fumarate, and citrate, which are precursors of succinate, 2-oxogluterate, valine, leucine, and isoleucine. The production of valine, leucine, formate, and pyruvate also obviates the need to supplement culture media with these compounds, which may result in further cost savings. Furthermore, reduction or elimination of lactate production by a bacterium reduces or eliminates the toxic effects of lactate on the bacterium.

The invention provides a carboxydotrophic acetogenic bacterium comprising a disrupting mutation in a lactate biosynthesis pathway enzyme.

"Mutation" refers to a modification in a nucleic acid or protein in the bacterium of the invention compared to the wild-type or parental microorganism from which the bacterium of the invention is derived. The term "genetic modification" encompasses the term "mutation." In one embodiment, the mutation may be a deletion, insertion, or substitution of one or more nucleotides in a gene encoding an enzyme. In another embodiment, the mutation may be a deletion, insertion, or substitution of one or more amino acids in an enzyme.

Typically, the mutation is a "disrupting mutation" that reduces or eliminates (i.e., "disrupts") the expression or activity of a lactate biosynthesis pathway enzyme. The disrupting mutation may partially inactivate, fully inactivate, or delete a lactate biosynthesis pathway enzyme or a gene encoding the enzyme. The disrupting mutation may be a knockout (KO) mutation. The disrupting mutation may be any mutation that reduces, prevents, or blocks the biosynthesis of lactate. The disrupting mutation may include, for example, a mutation in a gene encoding a lactate biosynthesis pathway enzyme, a mutation in a genetic regulatory element involved in the expression of a gene encoding a lactate biosynthesis pathway enzyme, the introduction of a nucleic acid which produces a protein that reduces or inhibits the activity of a lactate biosynthesis pathway enzyme, or the introduction of a nucleic acid (e.g., antisense RNA, siRNA, CRISPR) or protein which inhibits the expression of a lactate biosynthesis pathway enzyme.

The disrupting mutation results in a bacterium of the invention that produces no lactate or substantially no lactate or a reduced amount of lactate compared to the parental bacterium from which the bacterium is derived. For example, the bacterium of the invention may produce no lactate or at least about 1%, 3%, 5%, 10%, 20%, 30%, 40%, 50%, 60%, 70%, 80%, 90%, or 95% less lactate than the parental bacterium. For example, the bacterium of the invention may produce less than about 0.001, 0.01, 0.10, 0.30, 0.50, or 1.0 g/L lactate. In contrast, depending on fermentation conditions, unmodified *C. autoethanogenum* LZ1561 may produce up to about 2 g/L lactate. Other unmodified bacterial strains may produce even more lactate.

The disrupting mutation may be introduced using any method known in the art. Exemplary methods include heterologous gene expression, gene or promoter insertion or deletion, altered gene expression or inactivation, enzyme engineering, directed evolution, knowledge-based design, random mutagenesis methods, gene shuffling, and codon optimization. Such methods are described, for example, in Sambrook, Molecular Cloning: A Laboratory Manual, Cold Spring Harbor Laboratory Press, Cold Spring Harbor, NY, 2001; Pleiss, *Curr Opin Biotechnol,* 22: 611-617, 2011; and Park, Protein Engineering and Design, CRC Press, 2010. The disrupting mutation may be introduced using nucleic acids, such as single-stranded or double-stranded DNA, RNA, cDNA, or combinations thereof, as is appropriate. The nucleic acids may be referred to as constructs or vectors, and may include one or more regulatory elements, origins of replication, multicloning sites, and/or selectable markers. In one embodiment, the nucleic acid may be adapted to disrupt a gene encoding a lactate biosynthesis pathway enzyme in a parental bacterium. In one embodiment, the nucleic acid may be adapted to allow expression of one or more genes encoded by the nucleic acid. Constructs or vectors may include plasmids (e.g., pMTL, pIMP, pJIR), viruses (including bacteriophages), cosmids, and artificial chromosomes. The constructs may remain extra-chromosomal upon transformation of a parental bacterium or may be adapted for integration into the genome of the bacterium. Accordingly, constructs may include nucleic acid sequences adapted to assist integration (e.g., a region which allows for homologous recombination and targeted integration into the host genome) or expression and replication of an extrachromosomal construct (e.g., origin of replication, promoter, and other regulatory sequences).

The nucleic acids may be introduced using homologous recombination. Such nucleic acids may include arms homologous to a region within or flanking the gene to be disrupted ("homology arms"). These homology arms allow homologous recombination and the introduction, deletion, or substitution of one or more nucleotides within the gene to be disrupted. While it is preferred that the homology arms have 100% complementarity to the target region in the genome, 100% complementarity is not required so long that the sequence is sufficiently complementary to allow for targeted recombination with the target region in the genome. Typically, the homology arms will have a level of homology which would allow for hybridization to a target region under stringent conditions (Sambrook, Molecular Cloning: A Laboratory Manual, Cold Spring Harbor Laboratory Press, Cold Spring Harbor, N.Y., 1989). Knowledge of the target nucleic acid sequences in a parental bacterium (i.e., the sequence of a target gene or target region in a parental bacterium) is generally sufficient to design appropriate homology arms. For example, to disrupt LDH, the flanking homology arms described herein may be used (e.g., SEQ ID NOs: 1-2). In *C. ljungdahlii,* homology arms may be designed based on GenBank CP001666.1. For other strains, homology arms may be designed based on other publically available nucleic acid sequence information.

The "lactate biosynthesis pathway" is a pathway of reactions resulting in the production of lactate. In one embodiment, the lactate biosynthesis pathway comprises one or more enzymes that convert pyruvate to lactate. In one embodiment, the lactate biosynthesis pathway comprises a lactate dehydrogenase enzyme. Depending on the bacterium, a number of different enzymes may be involved in the lactate biosynthesis pathway. When a bacterium comprises two or more enzymes in the lactate biosynthesis pathway, e.g., two or more enzymes capable of converting pyruvate to lactate, disrupting more than one such enzyme may have the effect of increasing the production of a product above the level that may be achieved by disrupting a single enzyme. In one embodiment, the bacterium comprises disrupting mutations in two, three, four, five, or more enzymes capable of converting pyruvate to lactate. While disrupting expression and/or activity of all such enzymes may provide some advantage in terms of product production, it is not generally necessary to disrupt expression and/or activity of all such enzymes to gain the benefits of the invention, namely increased production of one or more main or target products.

In one embodiment, the lactate biosynthesis pathway enzyme natively (i.e., endogenously or naturally) converts pyruvate to lactate, such that the enzyme has lactate dehydrogenase activity. The enzyme may have additional catalytic functions so long as it also converts pyruvate to lactate. For example, the enzyme may be any dehydrogenase having lactate dehydrogenase activity. The introduction of a disrupting mutation to the enzyme that converts pyruvate to lactate reduces or eliminates (i.e., "disrupts") the expression or activity of that enzyme.

In a preferred embodiment, the lactate biosynthesis pathway enzyme is lactate dehydrogenase (LDH). The introduction of a disrupting mutation to LDH reduces or eliminates (i.e., "disrupts") the expression or activity of LDH.

The bacterium of the invention may comprise one or more other genetic modifications in addition to a disrupting mutation in a lactate biosynthesis pathway enzyme, including genetic modifications of one or more genes or proteins not associated with the lactate biosynthesis pathway.

In one particular embodiment, the bacterium of the invention may express an inhibitor of a lactate biosynthesis pathway enzyme in addition to or instead of comprising a disrupting mutation in a lactate biosynthesis pathway enzyme.

"Enzyme activity" refers broadly to enzymatic activity, including, but not limited to, the activity of an enzyme, the amount of an enzyme, or the availability of an enzyme to catalyze a reaction. Accordingly, "decreasing" or "reducing" enzyme activity includes decreasing or reducing the activity of an enzyme, the amount of an enzyme, or the availability of an enzyme to catalyze a reaction. An enzyme is "capable of converting" a first compound or substrate into a second compound or product, if it can catalyze a reaction in which at least a portion of the first compound is converted into the second compound.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Variant nucleic acids or proteins with substantially the same level of activity as a reference nucleic acid or protein may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also includes nucleic acids whose sequence varies as a result of codon optimization for a particular organism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

However, variant nucleic acids or proteins may also have a reduced level of activity compared to a reference nucleic acid or protein. For example, a variant nucleic acid may have a reduced level of expression or a variant enzyme may have a reduced ability to catalyze a particular reaction compared to a reference nucleic acid or enzyme, respectively. Enzyme assays and kits for assessing the activity of enzymes in the lactate biosynthesis pathway are known in the art (Wang, *J Bacteriol*, 195: 4373-4386, 2013; Sigma-Aldrich (MAK066), Thermo (88953); Worthington Biochemical Corporation (LS002755)).

Nucleic acids may be delivered to a bacterium of the invention using any method known in the art. For example, nucleic acids may be delivered as naked nucleic acids or may be formulated with one or more agents (e.g., liposomes). Restriction inhibitors may be used in certain embodiments (Murray, *Microbiol Molec Biol Rev*, 64: 412-434, 2000). By way of example, transformation (including transduction or transfection) may be achieved by electroporation, ultrasonication, polyethylene glycol-mediated transformation, chemical or natural competence, protoplast transformation, prophage induction, or conjugation (see, e.g., Sambrook, Molecular Cloning: A Laboratory Manual, Cold Spring Harbor Laboratory Press, Cold Spring Harbor, N.Y., 1989). The use of electroporation has been reported for several carboxydotrophic acetogens, including *Clostridium ljungdahlii* (Koepke, PNAS, 107:13087-13092, 2010; WO/2012/053905), *Clostridium autoethanogenum* (WO/2012/053905), *Clostridium aceticum* (Schiel-Bengelsdorf, *Synthetic Biol*, 15: 2191-2198, 2012), and *Acetobacterium woodii* (Strätz, *Appl Environ Microbiol*, 60: 1033-1037, 1994). The use of electroporation has also been reported in *Clostridia*, including *Clostridium acetobutylicum* (Mermelstein, *Biotechnol*, 10: 190-195, 1992), and *Clostridium cellulolyticum* (Jennert, Microbiol, 146: 3071-3080, 2000). Prophage induction has been demonstrated for carboxydotrophic acetogens, including *Clostridium scatologenes* (Parthasarathy, Development of a Genetic Modification System in *Clostridium scatologenes* ATCC 25775 for Generation of Mutants, Masters Project, Western Kentucky University, 2010), and conjugation been described for many *Clostridia*, including *Clostridium difficile* (Herbert, *FEMS Microbiol Lett*, 229: 103-110, 2003) and *Clostridium acetobuylicum* (Williams, *J Gen Microbiol*, 136: 819-826, 1990). In certain embodiments having active restriction enzyme systems, it may be necessary to methylate a nucleic acid before introduction of the nucleic acid into the bacterium of the invention (WO 2012/105853).

The term "recombinant" indicates that a nucleic acid, protein, or microorganism is the product of genetic modification, mutation, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

A "parental bacterium" is a bacterium used to generate a bacterium of the invention. The parental bacterium may be a naturally-occurring bacterium (i.e., a wild-type bacterium) or a bacterium that has been previously modified (i.e., a mutant or recombinant bacterium). The bacterium of the invention may be modified to express a lower amount of an enzyme compared to the parental bacterium, or the bacterium of the invention may be modified to not express an enzyme that is expressed by the parental bacterium. In one embodiment, the parental bacterium is *Clostridium autoethanogenum*, *Clostridium ljungdahlii*, or *Clostridium rag-*

*sdalei*. In a preferred embodiment, the parental bacterium is *Clostridium autoethanogenum* deposited under DSMZ accession DSM23693 (i.e., *Clostridium autoethanogenum* LZ1561).

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the bacterium of the invention is derived from a parental bacterium. In one embodiment, the bacterium of the invention is derived from *Clostridium autoethanogenum*, *Clostridium ljungdahlii*, or *Clostridium ragsdalei*. In a preferred embodiment, the bacterium of the invention is derived from *Clostridium autoethanogenum* LZ1561, which is deposited under DSMZ accession DSM23693.

In one embodiment, the parental bacterium is selected from the group of carboxydotrophic acetogenic bacteria comprising the species *Clostridium autoethanogenum, Clostridium ljungdahlii, Clostridium ragsdalei, Clostridium coskatii, Clostridium carboxidivorans, Clostridium drakei, Clostridium scatologenes, Clostridium aceticum, Clostridium formicoaceticum, Clostridium magnum, Acetobacterium woodii, Alkalibaculum bacchii, Moorella thermoacetica, Sporomusa ovate, Butyribacterium methylotrophicum, Blautia producta, Eubacterium limosum,* and *Thermoanaerobacter kiuvi*. These carboxydotrophic acetogenic bacteria are defined by their ability to grow chemoautotrophically on gaseous one-carbon sources such as carbon monoxide (CO) and carbon dioxide ($CO_2$), use carbon monoxide (CO) and/or hydrogen ($H_2$) as energy sources under anaerobic conditions, and produce acetyl-CoA, acetate, and other products. They share the same mode of fermentation, the Wood-Ljungdahl or reductive acetyl-CoA pathway, and are defined by the presence of the enzyme set consisting of carbon monoxide dehydrogenase (CODH), hydrogenase, formate dehydrogenase, formyl-tetrahydrofolate synthetase, methylene-tetrahydrofolate dehydrogenase, formyl-tetrahydrofolate cyclohydrolase, methylene-tetrahydrofolate reductase, and carbon monoxide dehydrogenase/acetyl-CoA synthase (CODH/ACS), which combination is characteristic and unique to this type of bacteria (Drake, The Prokaryotes, 354-420, Springer, New York, N.Y., 2006). In contrast to chemoheterotrophic growth of sugar-fermenting bacteria that convert a substrate into biomass, secondary metabolites, and pyruvate, from which products are formed directly or via acetyl-CoA, acetogens channel a substrate directly into acetyl-CoA, from which products, biomass, and secondary metabolites are formed.

In a preferred embodiment, the bacterium of the invention is derived from a parental microorganism comprising a lactate dehydrogenase, wherein the bacterium of the invention comprises a disrupting mutation in the lactate dehydrogenase. For example, the parental microorganism may be *C. autoethanogenum* comprising a nucleic acid sequence comprising GenBank AEI90736.1 or an amino acid sequence comprising GenBank CP006763.1, KEGG CAETHG_1147, or GenBank HQ876025.1. The parental microorganism may be *C. ljungdahlii* comprising a nucleic acid sequence comprising GenBank YP_003781368.1 or an amino acid sequence comprising GenBank CP001666.1 or KEGG CLJU_c32190. The parental microorganism may be *C. ragsdalei* comprising a nucleic acid sequence comprising GenBank AEI90737.1 or an amino acid sequence comprising GenBank HQ876026.1. Other parental bacteria may have other nucleic acid and amino acid sequences.

A "carboxydotroph" is a microorganism capable of tolerating a high concentration of carbon monoxide (CO). Typically, the bacterium of the invention is a carboxydotroph.

The bacterium of the invention may be derived from the cluster of carboxydotrophic *Clostridia* comprising the species *Clostridium autoethanogenum, Clostridium ljungdahlii, Clostridium ragsdalei*, and related isolates, including, but not limited to, strains *Clostridium autoethanogenum* JAI-1T (DSM10061) (Abrini, Arch Microbiol, 161: 345-351, 1994), *Clostridium autoethanogenum* LBS1560 (DSM19630) (WO 2009/064200), *Clostridium autoethanogenum* LZ1561 (DSM23693), *Clostridium ljungdahlii* PETCT (DSM13528=ATCC 55383) (Tanner, Int J Syst Bacteriol, 43: 232-236, 1993), *Clostridium ljungdahlii* ERI-2 (ATCC 55380) (U.S. Pat. No. 5,593,886), *Clostridium ljungdahlii* C-01 (ATCC 55988) (U.S. Pat. No. 6,368,819), *Clostridium ljungdahlii* 0-52 (ATCC 55989) (U.S. Pat. No. 6,368,819), *Clostridium ragsdalei* P11T (ATCC BAA-622) (WO 2008/028055), related isolates such as "*Clostridium coskatii*" (U.S. Publication 2011/0229947), or mutated strains such as *Clostridium ljungdahlii* OTA-1 (Tirado-Acevedo, Production of Bioethanol from Synthesis Gas Using *Clostridium ljungdahlii*, PhD thesis, North Carolina State University, 2010).

These strains form a subcluster within the Clostridial rRNA cluster I and their 16S rRNA gene is more than 99% identical with a similar low GC content of around 30%. However, DNA-DNA reassociation and DNA fingerprinting experiments showed that these strains belong to distinct species (WO 2008/028055). The strains of this cluster are defined by common characteristics, having both a similar genotype and phenotype, and they all share the same mode of energy conservation and fermentative metabolism. Furthermore, the strains of this cluster lack cytochromes and conserve energy via an Rnf complex. All species of this cluster have a similar morphology and size (logarithmic growing cells are between 0.5-0.7×3-5 µm), are mesophilic (optimal growth temperature between 30-37° C.), and are strictly anaerobic (Abrini, *Arch Microbiol*, 161: 345-351, 1994; Tanner, *Int J Syst Bacteriol*, 43: 232-236, 1993; and WO 2008/028055). Moreover, they all share the same major phylogenetic traits, such as same pH range (pH 4-7.5, with an optimal initial pH of 5.5-6), strong autotrophic growth on CO-containing gases with similar growth rates, and a similar metabolic profile with ethanol and acetic acid as main fermentation end products, and small amounts of 2,3-butanediol and lactic acid formed under certain conditions (Abrini, Arch Microbiol, 161: 345-351, 1994; Köpke, *Curr Opin Biotechnol*, 22: 320-325, 2011; Tanner, *Int J Syst Bacteriol*, 43: 232-236, 1993; and WO 2008/028055). Indole production was observed with all three species as well.

However, the species differentiate in substrate utilization of various sugars (e.g., rhamnose, arabinose), acids (e.g., gluconate, citrate), amino acids (e.g., arginine, histidine), or other substrates (e.g., betaine, butanol). Moreover, some of the species were found to be auxotrophic to certain vitamins (e.g., thiamine, biotin) while others were not. The organization and number of Wood-Ljungdahl pathway genes, responsible for gas uptake, has been found to be the same in all species, despite differences in nucleic and amino acid sequences (Köpke, *Curr Opin Biotechnol*, 22: 320-325, 2011). Also, reduction of carboxylic acids into their corresponding alcohols has been shown in a range of these microorganisms (Perez, *Biotechnol Bioeng*, 110:1066-1077, 2012). These traits are therefore not specific to one microorganism, like *Clostridium autoethanogenum* or *Clostridium ljungdahlii*, but rather general traits for carboxydotrophic, ethanol-synthesizing *Clostridia* and it can be anticipated that mechanisms work similarly across these strains, although there may be differences in performance.

An "acetogen" is a microorganism that generates or is capable of generating acetate as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In a preferred embodiment, the bacterium of the invention is an acetogen.

The invention further provides a method of producing a product comprising culturing the bacterium of the invention in the presence of a substrate comprising CO whereby the bacterium of the invention produces a product.

The term "substrate" refers to a carbon and/or energy source for the bacterium of the invention. Typically, the substrate is a gaseous substrate that comprises carbon monoxide (CO). The substrate may comprise a major proportion of CO, such as about 20% to 100%, 20% to 70%, 30% to 60%, or 40% to 55% CO by volume. In particular embodiments, the substrate comprises about 20%, 25%, 30%, 35%, 40%, 45%, 50%, 55%, or 60% CO by volume. The bacterium of the invention generally converts at least a portion of the CO in the substrate to a product.

While it is not necessary for the substrate to contain any hydrogen ($H_2$), the presence of $H_2$ should not be detrimental to product formation and may result improved overall efficiency. For example, in particular embodiments, the substrate may comprise an approximate ratio of $H_2$:CO of 2:1, 1:1, or 1:2. In one embodiment, the substrate comprises less than about 30%, 20%, 15%, or 10% $H_2$ by volume. In other embodiments, the substrate comprises low concentrations of $H_2$, for example, less than 5%, less than 4%, less than 3%, less than 2%, or less than 1% $H_2$. In further embodiments, the substrate contains substantially no $H_2$.

The substrate may also contain carbon dioxide ($CO_2$), for example, about 1% to 80% or 1% to 30% $CO_2$ by volume. In one embodiment, the substrate comprises less than about 20% $CO_2$ by volume. In further embodiments, the substrate comprises less than about 15%, 10%, or 5% $CO_2$ by volume. In another embodiment, the substrate contains substantially no $CO_2$.

Although the substrate is typically gaseous, the substrate may also be provided in alternative forms. For example, the substrate may be dissolved in a liquid saturated with a CO-containing gas using a microbubble dispersion generator (Hensirisak, *Appl Biochem Biotechnol*, 101: 211-227, 2002). By way of further example, the substrate may be adsorbed onto a solid support.

The substrate may be a waste gas obtained as a by-product of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the CO-containing gas may be captured from the industrial process before it is emitted into the atmosphere, using any convenient method. The CO may be a component of syngas, i.e., a gas comprising carbon monoxide and hydrogen. The CO produced from industrial processes is normally flared off to produce $CO_2$ and therefore the invention has particular utility in reducing $CO_2$ greenhouse gas emissions. The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The bacterium of the invention may be cultured to produce one or more products. Generally, the bacterium of the invention produces one or more products selected from the group consisting of ethanol, 2,3-butanediol, formate, pyruvate, succinate, valine, leucine, isoleucine, malate, fumarate, 2-oxogluterate, citrate, and citramalate. The bacterium of the invention may also produce other products, such as acetolactate or acetoin malate.

In a preferred embodiment, the bacterium of the invention produces an increased amount of one or more of ethanol, 2,3-butanediol, formate, pyruvate, succinate, valine, leucine, isoleucine, malate, fumarate, 2-oxogluterate, citrate, and citramalate compared to a parental bacterium. For example, the bacterium of the invention may produce about 1%, 3%, 5%, 10%, 15%, 20%, 25%, 30%, 35%, 40%, 45%, 50%, 60%, 70%, 80%, 90%, 100%, 150%, 200%, 300%, 400%, or 500% more of one or more products compared to the parental bacterium from which the bacterium of the invention is derived. This increase in product production may be due, at least in part, to the disrupting mutation in the lactate biosynthesis pathway enzyme, which diverts carbon and energy away from the production of lactate and towards the production of other products.

The term "main product" refers to the single product produced in the highest concentration and/or yield. In one embodiment, the main product is ethanol or 2,3-butanediol.

Additionally, it is possible to engineer the bacterium of the invention to favor the production of one or more products over one or more other products. For example, disrupting the conversion of pyruvate to lactate may favor the production of 2,3-butanediol, formate, malate, fumarate, citrate, succinate and 2-oxogluterate over the production of valine, leucine and isoleucine.

Herein, recitation of a product (e.g., citrate) includes both salt (e.g., citrate) and acid (e.g., citric acid) forms of the product. Oftentimes, a mixture of the salt and acid forms of the product will be present in a fermentation broth, in a ratio that varies depending on the pH of the broth. As further examples, the term "acetate" encompasses acetate and acetic acid, the term "formate" encompasses formate and formic acid, the term "malate" encompasses malate and malic acid, and the term "lactate" encompasses lactate and lactic acid.

Unless the context requires otherwise, reference to any compound herein which may exist in one or more isomeric forms (for example, D, L, meso, S, R, cis, or trans forms) should be taken generally to encompass any one or more such isomers of the compound. For example, reference to "lactate" generally encompasses both the D and L isomers of lactate.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the bacterium. Preferably the aqueous culture medium is a minimal anaerobic microbial growth medium. Suitable media are known in the art and described, for example, in U.S. Pat. No. 5,173,429, U.S. Pat. No. 5,593,886, and WO 2002/008438.

The culture/fermentation should desirably be carried out under appropriate conditions for production of the target product. Reaction conditions to consider include pressure (or partial pressure of CO), temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. In particular, the rate of introduction of the CO-containing substrate may be controlled to ensure that the concentration of CO in the liquid phase does not become limiting, since products may be consumed by the culture under CO-limited conditions.

The terms "increasing the efficiency," "increased efficiency," and the like, when used in relation to a fermentation process, include, but are not limited to, increasing one or more of the rate of growth of microorganisms catalyzing the fermentation, the growth and/or product production rate, the volume of desired product (such as alcohols) produced per volume of substrate consumed, the rate of production or level of production of the desired product, and the relative proportion of the desired product produced compared with other by-products of the fermentation.

Operating a bioreactor at elevated pressures allows for an increased rate of CO mass transfer from the gas phase to the liquid phase. Accordingly, it is generally preferable to perform the culture/fermentation at pressures higher than atmospheric pressure. Also, since a given CO conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. According to examples in U.S. Pat. No. 5,593,886, reactor volume can be reduced in linear proportion to increases in reactor operating pressure. In other words, a bioreactor operated at 10 atmospheres of pressure need only be one tenth the volume of a bioreactor operated at 1 atmosphere of pressure. Additionally, WO 2002/008438 describes gas-to-ethanol fermentations performed under pressures of 30 psig and 75 psig, giving ethanol productivities of 150 g/L/day and 369 g/L/day, respectively. In contrast, fermentations performed using similar media and input gas compositions at atmospheric pressure were found to produce between 10 and 20 times less ethanol per litre per day.

The method of the invention may further comprise recovering or purifying one or more products. For example, ethanol or a mixed alcohol stream containing ethanol and/or other products may be recovered from a fermentation broth by any method known in the art, including fractional distillation, evaporation, pervaporation, or extractive fermentation (e.g., liquid-liquid extraction). Byproducts, such as acetate or acids, may also be recovered from a fermentation broth using any method known in the art, including activated charcoal adsorption systems, electrodialysis, or continuous gas stripping. In one embodiment, a product may be recovered from a fermentation broth by continuously removing a portion of the broth from the bioreactor, separating microbial cells from the broth (conveniently by filtration), and recovering the product from the broth. The separated microbial cells may be returned to the bioreactor. Additionally, cell-free permeate may also be returned to the bioreactor after the product has been removed, optionally with supplementation of nutrients, such as B vitamins.

Succinate can be recovered from a fermentation broth using, for example, acidification, electrodialysis coupled with ion-exchange chromatography (Song, *Enzyme Microb Technol*, 39: 352-361, 2006), precipitation with Ca(OH) coupled with filtration and addition of sulfuric acid (Lee, *Appl Microbiol Biotechnol*, 79: 11-22, 2008), or reactive extraction with amine-based extractants such as tri-n-octylamine (Huhp, *Proc Biochem* 41: 1461-1465, 2006). For all methods, it is crucial to have the free acid form, not the salt. Most biotechnological production processes for succinic acid, however, operate at a neutral or slightly acidic pH of 6-7. Given the pKa of succinic acid (pKa =4.16 and 5.61), the majority of succinic acid is present as salt and not as free acid under these conditions. *C. autoethanogenum* and other carboxydotrophic acetogens, however, are known to tolerate and grow at a desirably low pH of 4-6.

Branched-chain amino acids, such as valine, leucine, and isoleucine, may be recovered from a fermentation broth using concentration (e.g., via reverse osmosis), crystallization or removal of the biomass (e.g., via ultrafiltration or centrifugation), or ion exchange chromatography (Ikeda, Microbial Production of L-Amino Acids, 1-35, 2003).

2,3-butanediol, formate, 2-oxogluterate, and other products may be recovered from a fermentation broth using any method known in the art. For example, low concentrations of 2,3-butanediol may be recovered using membrane techniques, such as electrodialysis, involving the application of a suitable potential across a selective ion permeable membrane. Other suitable techniques include nanofiltration, wherein monovalent ions selectively pass through a membrane under pressure.

EXAMPLES

The following examples further illustrate the invention but, of course, should not be construed to limit its scope in any way.

Example 1

This example describes general materials and methods.

*C. autoethanogenum* DSM10061 and DSM23693 (a derivate of DSM10061) and *C. ljungdahlii* DSM13528 were sourced from DSMZ (The German Collection of Microorganisms and Cell Cultures, Inhoffenstraße 7 B, 38124 Braunschweig, Germany). *C. ragsdalei* ATCC BAA-622 was sourced from ATCC (American Type Culture Collection, Manassas, Va. 20108, USA). *E. coli* DH5α was sourced from Invitrogen (Carlsbad, Calif. 92008, USA).

*E. coli* was grown aerobic at 37° C. in LB (Luria-Bertani) medium. Solid media contained 1.5% agar.

| LB medium component | Amount per 1.0 L of LB medium |
|---|---|
| Tryptone | 10 g |
| Yeast extract | 5 g |
| NaCl | 10 g |

*Clostridium* strains were grown at 37° C. in PETC medium at pH 5.6 using standard anaerobic techniques (Hungate, *Methods Microbiol,* 3B: 117-132, 1969; Wolfe, *Adv Microbiol Physiol,* 6: 107-146, 1971). Fructose (heterotrophic growth) or 30 psi CO-containing steel mill gas (collected from New Zealand Steel site in Glenbrook, NZ; composition: 44% CO, 32% N2, 22% $CO_2$, 2% $H_2$) in the headspace (autotrophic growth) was used as substrate. For solid media, 1.2% bacto agar (BD, Franklin Lakes, N.J. 07417, USA) was added.

| PETC medium component | Amount per 1.0 L of PETC medium |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution (see below) | 10 ml |
| Wolfe's vitamin solution (see below) | 10 ml |
| Yeast extract (optional) | 1 g |
| Resazurin (2 g/L stock) | 0.5 ml |
| $NaHCO_3$ | 2 g |
| Reducing agent solution (see below) | 0.006-0.008% (v/v) |
| Fructose (for heterotrophic growth) | 5 g |

| Trace metal solution component | Amount per 1.0 L of trace metal solution |
|---|---|
| Nitrilotriacetic acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |

| Wolfe's vitamin solution component | Amount per 1.0 L of Wolfe's vitamin solution |
|---|---|
| Biotin | 2 mg |
| Folic acid | 2 mg |
| Pyridoxine hydrochloride | 10 mg |
| Thiamine HCl | 5 mg |
| Riboflavin | 5 mg |
| Nicotinic acid | 5 mg |
| Calcium D-(+)-pantothenate | 5 mg |
| Vitamin B12 | 0.1 mg |
| P-aminobenzoic acid | 5 mg |
| Thioctic acid | 5 mg |

| Reducing agent solution component | Amount per 100 mL of reducing agent solution |
|---|---|
| NaOH | 0.9 g |
| Cysteine-HCl | 4 g |
| $Na_2S$ | 4 g |

Fermentations with *C. autoethanogenum* DSM23693 were carried out in 1.5 L bioreactors at 37° C. using CO-containing steel mill gas as sole energy and carbon source. A defined medium was prepared, containing: $MgCl_2$ $CaCl_2$ (0.5 mM), KCl (2 mM), $H_3PO_4$ (5 mM), Fe (100 μM), Ni, Zn (5 μM), Mn, B, W, Mo, Se (2 μM). The medium was transferred into the bioreactor and autoclaved at 121° C. for 45 minutes. After autoclaving, the medium was supplemented with thiamine, pantothenate (0.05 mg/l), and biotin (0.02 mg/l) and reduced with 3 mM cysteine-HC1. To achieve anaerobic conditions, the reactor vessel was sparged with nitrogen through a 0.2 p.m filter. Prior to inoculation, the gas was switched to CO-containing steel mill gas, feeding continuously to the reactor. The gas flow was initially set at 80 ml/min and increased to 200 ml/min during mid-exponential phase, while the agitation was increased from 200 rpm to 350 rmp. $Na_2S$ was dosed into the bioreactor at 0.25 ml/hr. Once the OD600 reached 0.5, the bioreactor was switched to continuous mode at a rate of 1.0 ml/min (dilution rate 0.96 $d^{-1}$). Samples were taken to measure the biomass and metabolites. Additionally, headspace analysis of the in- and out-flowing gas was performed on regular basis.

Gas composition of the headspace was measured on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

HPLC analysis of metabolic end products was performed using an Agilent 1100 Series HPLC system equipped with a RID (Refractive Index Detector) operated at 35° C. and an Alltech IOA-2000 organic acid column (150×6.5 mm, particle size 5 μm) kept at 60° C. Slightly acidified water was used (0.005 M $H_2SO_4$) as mobile phase with a flow rate of 0.7 ml/min. To remove proteins and other cell residues, 400 μl samples were mixed with 100 μl of a 2% (w/v) 5-sulfosalicylic acid and centrifuged at 14,000×g for 3 min to separate precipitated residues. 10 μl of the supernatant were then injected into the HPLC for analyses.

GC analysis of metabolic end products was performed using an Agilent 6890N headspace GC equipped with a Supelco PDMS 100 1cm fiber, an Alltech EC-1000 (30 m×0.25 mm×0.25 μm) column, and a flame ionization detector (FID). 5 ml samples were transferred into a Hungate tube, heated to 40° C. in a water bath and exposed to the fiber for exactly 5 min. The injector was kept at 250° C. and helium with a constant flow of 1 ml/min was used as carrier gas. The oven program was 40° C. for 5 min, followed by an increase of 10° C./min up to 200° C. The temperature was then further increased to 220° C. with a rate of 50° C./min followed by a 5 min hold at this temperature, before the temperature was decreased to 40° C. with a rate of 50° C./min and a final 1 min hold. The FID was kept at 250° C. with 40 ml/min hydrogen, 450 ml/min air and 15 ml/min nitrogen as make up gas.

During the complete transformation experiment, *C. autoethanogenum* DSM23693 was grown in YTF medium in the presence of reducing agents and with 30 psi steel mill waste gas (collected from New Zealand Steel site in Glenbrook, NZ; composition: 44% CO, 32% $N_2$, 22% $CO_2$, 2% $H_2$) at 37° C. using standard anaerobic techniques (Hungate, *Methods Microbiol,* 3B: 117-132, 1969; Wolfe, *Adv Microbiol Physiol,* 6: 107-146, 1971).

| YTF medium component | Amount per 1.0 L of YTF medium |
|---|---|
| Yeast extract | 10 g |
| Tryptone | 16 g |

| | |
|---|---|
| Sodium chloride | 0.2 g |
| Fructose | 10 g |
| Distilled water | to 1.0 L |

| Reducing agent solution component | Amount per 100 mL of reducing agent solution |
|---|---|
| NaOH | 0.9 g |
| Cysteine-HCl | 4 g |
| Na$_2$S | 4 g |
| Distilled water | to 100 ml |

To make competent cells, a 50 ml culture of *C. autoethanogenum* DSM23693 was subcultured to fresh YTF media for 5 consecutive days. These cells were used to inoculate 50 ml YTF media containing 40 mM DL-threonine at an OD$_{600\ nm}$ of 0.05. When the culture reached an OD$_{600\ nm}$ of 0.5, the cells were incubated on ice for 30 minutes and then transferred into an anaerobic chamber and harvested at 4,700×g and 4° C. The culture was twice washed with ice-cold electroporation buffer (270 mM sucrose, 1 mM MgCl$_2$, 7 mM sodium phosphate, pH 7.4) and finally suspended in a volume of 600 µl fresh electroporation buffer. This mixture was transferred into a pre-cooled electroporation cuvette with a 0.4 cm electrode gap containing 2 µg of the methylated plasmid mix and 1 µl type 1 restriction inhibitor (Epicentre Biotechnologies) and immediately pulsed using the Gene pulser Xcell electroporation system (Bio-Rad) with the following settings: 2.5 kV, 600 Ω, and 25 µF. Time constants of 3.7-4.0 ms were achieved. The culture was transferred into 5 ml fresh YTF medium. Regeneration of the cells was monitored at a wavelength of 600 nm using a Spectronic Helios Epsilon Spectrophotometer (Thermo) equipped with a tube holder. After an initial drop in biomass, the cells started growing again. Once the biomass doubled from that point, about 200 µl of culture was spread on YTF-agar plates and PETC agar plates containing 5 g/l fructose (both containing 1.2% bacto agar and 15 µg/ml thiamphenicol). After 3-4 days of incubation with 30 psi steel mill gas at 37° C., 500 colonies per plate were clearly visible.

*C. autoethanogenum:* To verify the identity of the six clones and the DNA transfer, genomic DNA was isolated from all 6 colonies/clones in PETC liquid media using PURELINK™ Genomic DNA mini kit (Invitrogen) according to manufacturer's instruction. These genomic DNA along with that of wild-type *C. autoethanogenum* DSM23693 were used as a template in PCR. The PCR was performed with iproof High Fidelity DNA Polymerase (Bio-Rad Laboratories), specific primers as described in examples below and the following program: initial denaturation at 98° C. for 2 min, followed by 25 cycles of denaturation (98° C. for 10 s), annealing (61° C. for 15 s) and elongation (72° C. for 90 s), before a final extension step (72° C. for 7 min). The genomic DNA from wild-type *C. autoethanogenum* DSM23693 was used as template in control PCR.

To confirm the identity of the clones, PCR was also performed against the 16s rRNA gene using primers fD1 (SEQ ID NO: 10) and rP2 (SEQ ID NO: 11) and using PCR conditions as described above. The PCR products were purified using Zymo CLEAN AND CONCENTRATOR™ kit and sequenced using primer rP2.

Example 2

This example demonstrates the genetic modification of *C. autoethanogenum* to eliminate lactate dehydrogenase activity.

Demonstration of inactivation of the identified (Köpke, *Appl Environ Microbiol*, 77: 5467-5475, 2011) lactate dehydrogenase (AEI90736.1) gene ldh (HQ876025.1) of *C. autoethanogenum* was demonstrated by using two methodologies: homologous recombination and ClosTron.

Homologous recombination: To create a *C. autoethanogenum* strain that can no longer produce lactate, a knock out construct was designed to disrupt ldh by double homologous recombination. Approximately 1 kb homology arms (SEQ ID NOs: 1-2) flanking the ldh gene were cloned into pMTL85151 plasmid (FIG. 1) and the resulting plasmid pMTL85151-ldh-ko (SEQ ID NO: 3). Standard recombinant DNA and molecular cloning techniques are known in the art (Sambrook, Molecular Cloning: A Laboratory Manual, Cold Spring Harbor Laboratory Press, Cold Spring Harbor, N.Y., 2001; Ausubel, Current Protocols in Molecular Biology. Wiley, 1987). Genomic DNA from *C. autoethanogenum* DSM23693 was isolated using Purelink Genomic DNA mini kit from Invitrogen, according to the manufacturer's instruction.

Transformation to introduce DNA was carried out as described above or in WO 2012/053905.

Figure 2:
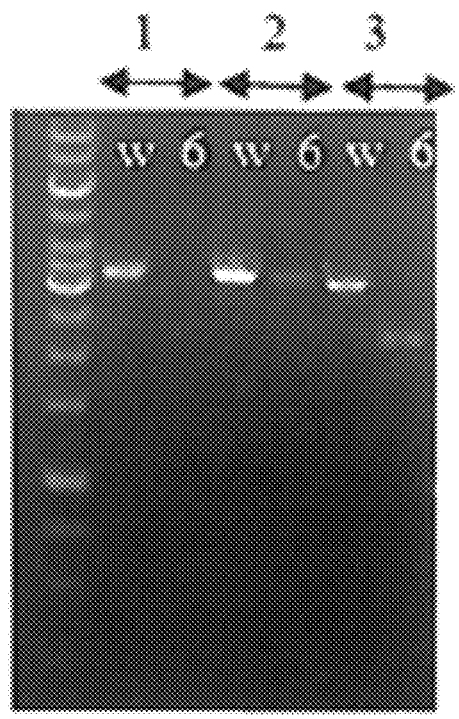
FIG. 2 is a set of gel images. The first gel image shows screening for single crossover integration of knockout plasmid using primers Og24r/Og35f for 5' crossover and Og21f/Og36r for 3' crossover in wild type (w) and transconjugant clone 6 (6). The second gel image shows screening for double crossover using outer flanking primers Og35f/Og36r and Og21f/Og24r.
Figure 2:
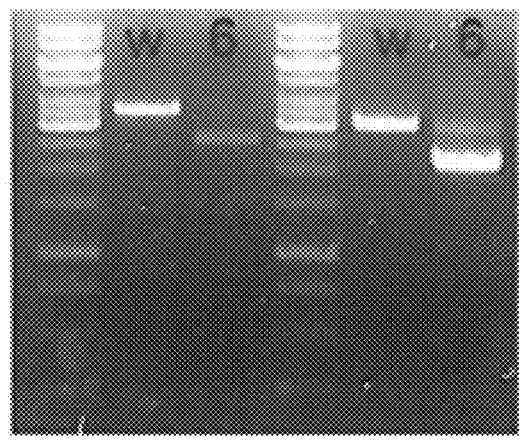

Following selection, colonies was screened for single crossover integration (FIG. 2A) and then for double-crossover mutants (FIG. 2B). A 3' crossover event was seen in clone 6 (FIG. 2A) and knockout of ldh gene was observed when screened with outer flanking primers (FIG. 2B). Oligonucleotides Og21f (SEQ ID NO: 4), Og24r (SEQ ID NO: 5), Og35f (SEQ ID NO: 6, and Og36r (SEQ ID NO: 7) were used for identification of the double-crossover lactate dehydrogenase deletion.

The same strategy and plasmid can also be used, for example, in *C. ljungdahlii* or *C. ragsdalei*. Transformation protocols have been described in the art (WO 2012/053905 Leang, *Applied Environ Microbiol*, 79: 1102-1109, 2013).

ClosTron: ClosTron (Heap, *J Microbiol Methods*, 70: 452-464, 2007), an intron design tool hosted on the ClosTron website, was used to design a 344 bp targeting region 129s (SEQ ID NO: 8) and identify a target site (SEQ ID NO: 9). The targeting region was chemically synthesized in the vector pMTL007C-E2 containing a retro-transposition activated ermB marker (RAM) by DNA2.0 (Menlo Park) (SEQ ID NO: 12).

Figure 3:
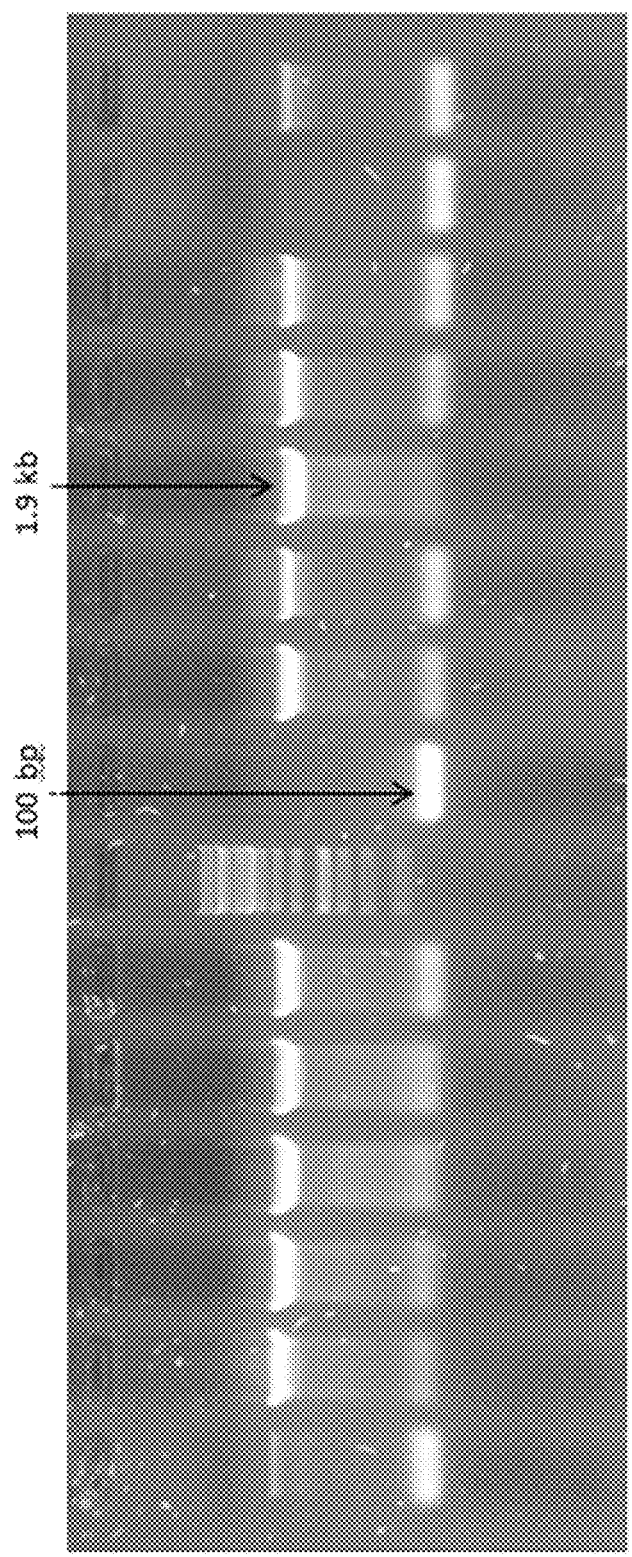
FIG. 3 is a gel image showing colony PCR for Gene ID: 126803 Target 129S using primers LdhAF/R. A PCR product of 100 bp indicated a wild-type genotype, while a product size of approximately 1.9 kb confirmed the insertion of the group II intron in the target site.
Figure 4:
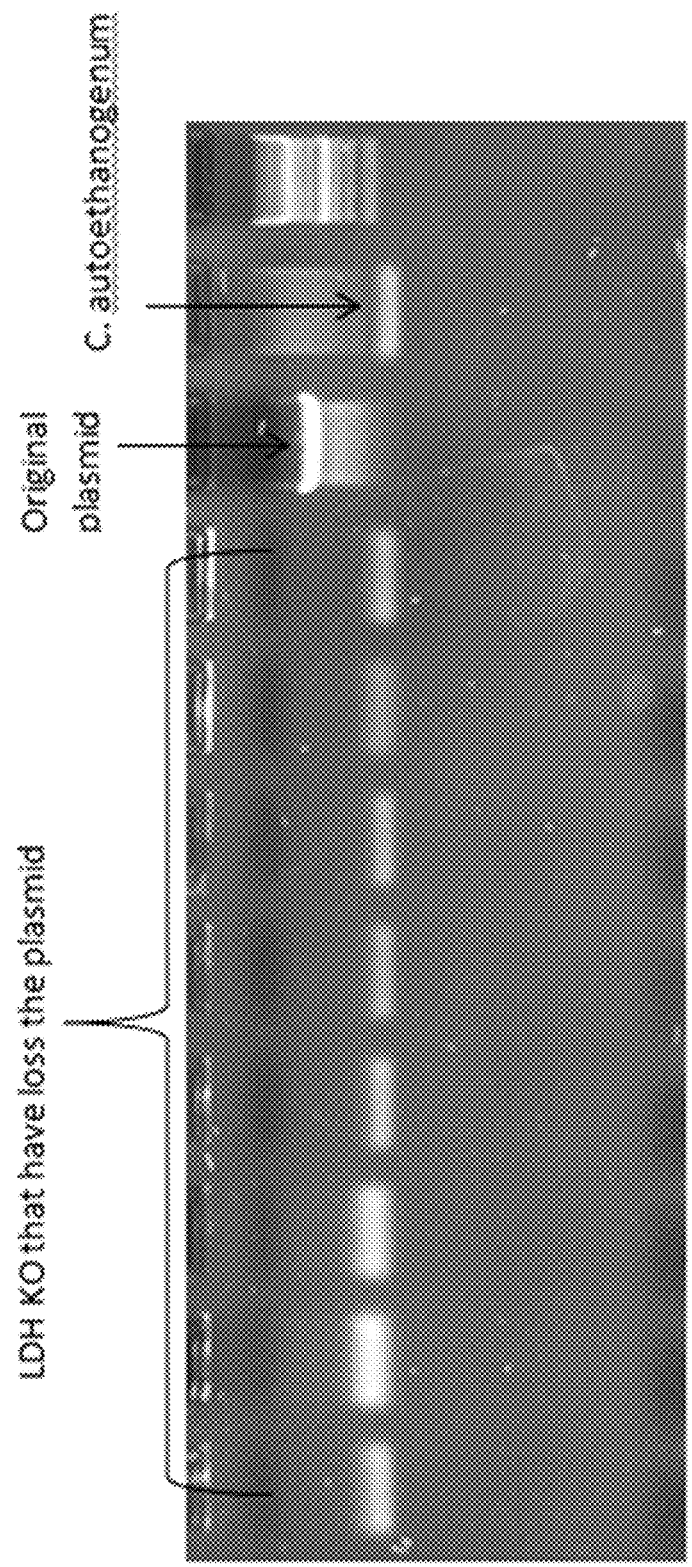
FIG. 4 is a gel image showing plasmid loss with primers CatPR/RepHF. The plasmid loss was checked by amplification of the resistance marker (catP) and the gram positive origin of replication (pCB102).

The vectors were introduced into *C. autoethanogenum* as described in WO 2012/053905. Single colonies grown on PETC MES with 15 µg/ml thiamphenicol were streaked on PETC MES with 5 µg/ml clarothromycin. Colonies from each target were randomly picked and screened for the insertion using flanking primers 155F (SEQ ID NO: 4), and 939R (SEQ ID NO: 5). Amplification was performed using the iNtron Maxime PCR premix. A PCR product of 100 bp indicated a wild-type genotype, while a product size of approximately 1.9 kb suggests the insertion of the group II intron in the target site (FIG. 3). The loss of the plasmid was checked by amplification of the resistance marker (catP) and the gram positive origin of replication (pCB102) (FIG. 4).

| SEQ ID NO | Description |
|---|---|
| 1 | left homology arm for disruption of the lactate dehydrogenase gene |
| 2 | right homology arm for disruption of the lactate dehydrogenase gene |
| 3 | plasmid pMTL85151-ldh-ko |
| 4 | oligonucleotide Og21f |
| 5 | oligonucleotide Og24r |
| 6 | oligonucleotide Og35f |

| SEQ ID NO | Description |
|---|---|
| 7 | oligonucleotide Og35f |
| 8 | ClosTron targeting region |
| 9 | ClosTron target site |
| 10 | oligonucleotide fD1 |
| 11 | oligonucleotide rP2 |
| 12 | ClosTron plasmid pMTL007C-E2-ldh::129s |

The same strategy and plasmid can also be used in *C. ljungdahlii* or *C. ragsdalei*. Transformation protocols have been described in the art (WO 2012/053905; Leang, *Appl Environ Microbiol*, 79: 1102-1109, 2013).

Example 3

This example describes growth experiments comparing the product profile of *C. autoethanogenum* strains with inactivated lactate dehydrogenase to unmodified *C. autoethanogenum*.

Cultures of *C. autoethanogenum* and a *C. autoethanogenum* strain with an inactivated lactate dehydrogenase were grown in PETC media with 10 g/L MES buffer in serum bottles. The inoculum was 10% of the media volume and the volume of the media was 10 ml. The cultures were gassed with steel mill off-gas (44% CO, 22% $CO_2$, 2% $H_2$, 32% $N_2$) 30 psi and incubated at 37° C. The pH of the media was 5.7.

During the growth period, samples were taken for the measurement of OD600 and for analysis by HPLC. The bottles were gassed every day with 30 psi mill gas. The experiment was performed in triplicate.

Figure 5A:
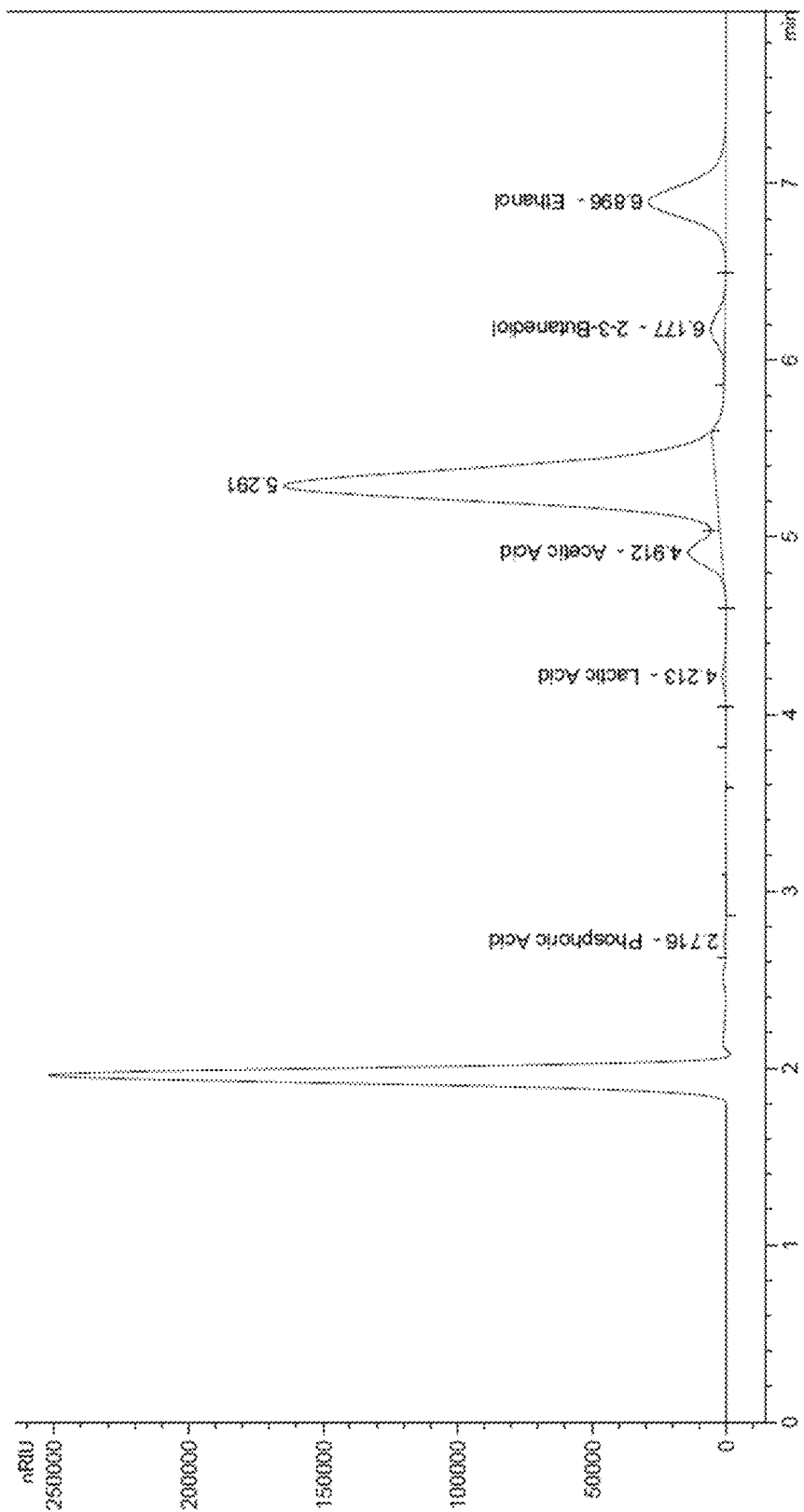
FIG. 5A is a graph showing HPLC analysis of *C. autoethanogenum* after 6 days of growth in serum bottles with 30 psi steel mill off-gas (44% CO, 22% $CO_2$, 2% $H_2$, 32% $N_2$) as substrate.
Figure 5B:
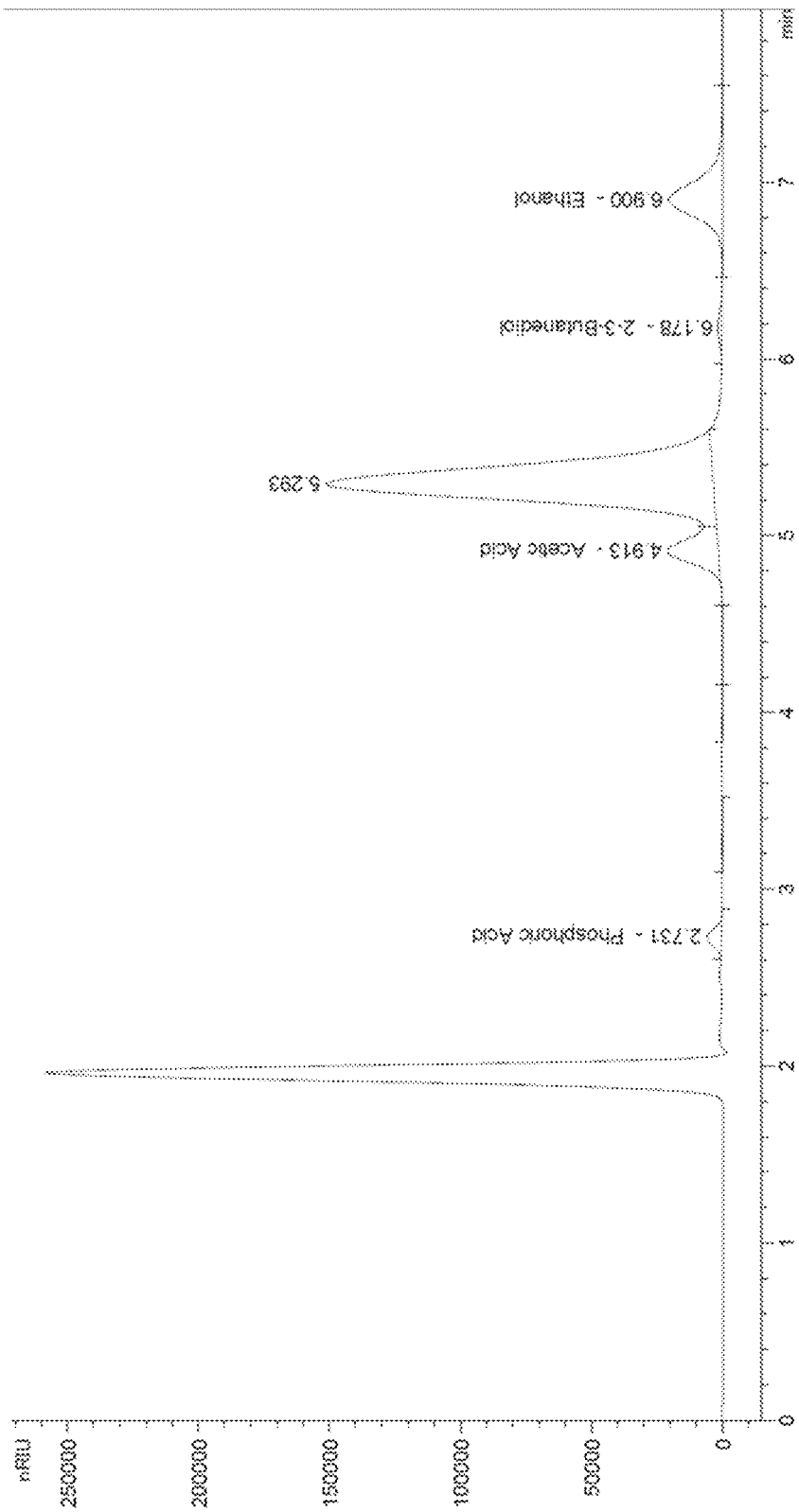
FIG. 5B is a graph showing HPLC analysis of *C. autoethanogenum* with inactivated lactate dehydrogenase after 6 days of growth in serum bottles with 30 psi steel mill off-gas (44% CO, 22% $CO_2$, 2% $H_2$, 32% $N_2$) as substrate.

While the unmodified *C. autoethanogenum* strain produced 0.263 ±0.041 g/L lactate after 6 days of growth (FIG. 5A), the *C. autoethanogenum* strain with inactivated lactate dehydrogenase produced no lactate after 6 days of growth (FIG. 5B). Additionally, the *C. autoethanogenum* strain with inactivated lactate dehydrogenase produced increased amounts of acetate, ethanol, and 2,3-butanediol. The two strains otherwise had a similar growth profile and reached a similar OD600nm of 2.69 and 2.365, respectively.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing a product comprising culturing a carboxydotrophic acetogenic bacterium comprising a disrupting mutation in a lactate dehydrogenase enzyme in the presence of a substrate comprising CO, $CO_2$, and/or $H_2$ whereby the bacterium produces a product selected from the group consisting of ethanol, 2,3-butanediol, formate, pyruvate, succinate, valine, leucine, isoleucine, malate, fumarate, 2-oxogluterate, citrate, and citramalate.

2. The method of claim 1, wherein the disrupting mutation reduces or eliminates the expression or activity of the enzyme.

3. The method of claim 1, wherein the disrupting mutation is a deletion of the lactate dehydrogenase enzyme or an inactivating mutation in the lactate dehydrogenase enzyme.

4. The method of claim 1, wherein the bacterium produces a reduced amount of lactate compared to a parental bacterium.

5. The method of claim 1, wherein the bacterium produces substantially no lactate.

6. The method of claim 1, wherein the product is ethanol.

7. The method of claim 1, wherein the bacterium produces an increased amount of the product compared to a parental bacterium.

8. The method of claim 7, wherein the product is selected from ethanol, 2,3-butanediol, formate, pyruvate, succinate, valine, leucine, isoleucine, malate, fumarate, 2-oxogluterate, citrate, and citramalate.

9. The method of claim 8, wherein the product is ethanol.

10. The method of claim 1, wherein the bacterium comprises a Wood-Ljungdahl pathway.

11. The method of claim 1, wherein the bacterium is derived from a parental bacterium selected from the group consisting of *Clostridium autoethanogenum*, *Clostridium ljungdahlii*, and *Clostridium ragsdalei*.

* * * * *